United States Patent
Lau et al.

(10) Patent No.: US 12,277,661 B2
(45) Date of Patent: Apr. 15, 2025

(54) THREE-DIMENSIONAL ANATOMICAL PARTS

(71) Applicant: Polymorph Medical, LLC, Durham, NC (US)

(72) Inventors: Trent Lau, Durham, NC (US); Rahul Ramesh, Chandler, AZ (US)

(73) Assignee: POLYMORPH MEDICAL, LLC, Miami, FL (US)

( * ) Notice: Subject to any disclaimer, the term of this patent is extended or adjusted under 35 U.S.C. 154(b) by 0 days.

(21) Appl. No.: 17/887,057

(22) Filed: Aug. 12, 2022

(65) Prior Publication Data

US 2023/0059287 A1 Feb. 23, 2023

Related U.S. Application Data

(60) Provisional application No. 63/232,744, filed on Aug. 13, 2021.

(51) Int. Cl.
| | |
|---|---|
| *G06T 17/00* | (2006.01) |
| *G06T 15/00* | (2011.01) |
| *G06T 15/08* | (2011.01) |
| *G06T 19/20* | (2011.01) |

(52) U.S. Cl.
CPC .............. *G06T 19/20* (2013.01); *G06T 15/08* (2013.01); *G06T 17/00* (2013.01); *G06T 2207/30004* (2013.01); *G06T 2207/30196* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 11,217,036 B1* | 1/2022 | Albuz | G06T 19/20 |
| 2013/0034276 A1* | 2/2013 | Hibbard | G06T 17/30 |
| | | | 382/128 |
| 2015/0250934 A1* | 9/2015 | Min | A61M 60/427 |
| | | | 700/119 |
| 2016/0155364 A1 | 6/2016 | Piron et al. | |
| 2016/0228255 A1* | 8/2016 | Samuelson | B22D 23/02 |
| 2017/0169733 A1 | 6/2017 | Peterson et al. | |
| 2017/0291359 A1 | 10/2017 | Kerins et al. | |
| 2018/0315348 A1 | 11/2018 | Dedmon et al. | |
| 2019/0147648 A1* | 5/2019 | Wolff | A61B 6/5247 |
| | | | 433/213 |
| 2020/0050119 A1* | 2/2020 | Shores | B22F 10/12 |
| 2022/0372748 A1* | 11/2022 | Hoch | B33Y 10/00 |

FOREIGN PATENT DOCUMENTS

| | | |
|---|---|---|
| CN | 104441664 A | 3/2015 |
| DE | 112006003722 B4 | 11/2008 |

\* cited by examiner

*Primary Examiner* — Joni Hsu
(74) *Attorney, Agent, or Firm* — Husch Blackwell LLP; Bryan D. Stewart

(57) ABSTRACT

Anatomical parts including surgical trainers and prosthesis and methods of creating three-dimensional anatomical parts by gathering three-dimensional image data from multiple sources, indexing characteristics from the data and then averaging the data to create new anatomical parts that have averaged characteristics. The disclosed methods also enable bonding of various materials through printed lattices.

13 Claims, 18 Drawing Sheets

FIG. 19
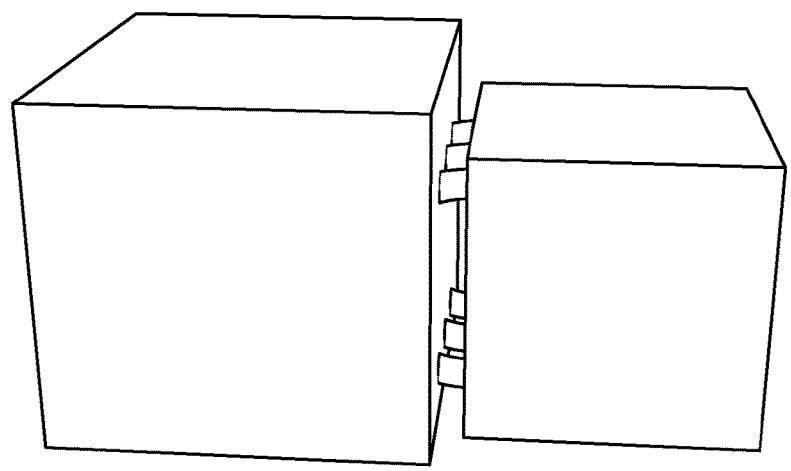
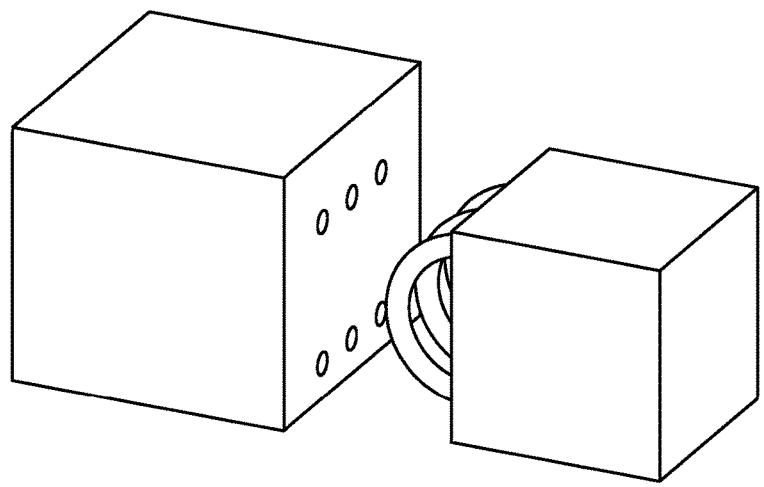
FIG. 20
FIG. 21
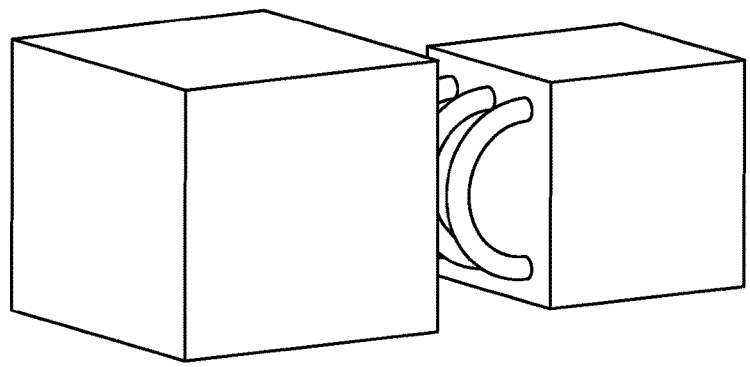

THREE-DIMENSIONAL ANATOMICAL PARTS

CROSS-REFERENCE TO RELATED APPLICATIONS

This patent application claims the benefit under 35 U.S.C. § 119(e) of U.S. Provisional Patent Application No. 63/232,744 filed Aug. 13, 2021 and titled Design and Manufacturing Process to Create Modular Surgical Simulators for Training, which application is incorporated herein by reference.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The invention relates to methods for medical training, surgical simulation, surgical practice, segmentation, three-dimensional (3D) Printing, biofidelic materials, three dimensional models, STL modification, slicing, medical imaging.

Description of the Related Art

Prior to the invention there was a noticeable gap in surgical training between first learning how to use surgical tools and learning surgical techniques and operating on patients. Medical school students and residents learn surgical skills by practicing with rudimentary equipment, including peg boards, silicone pads, and rubber tubes. With only this experience, they must transition to operating on patients over the course of many years, under the supervision of an attending surgeon. There are few opportunities to practice surgical operations and skills on relevant anatomy. A surgical resident must go from suturing a rubber tube that can be found in a hardware store to suturing wounds of patients with little to no opportunity to practice on something more advanced other than a rubber tube besides the occasional cadaver or animal carcass. Furthermore, cadavers and animal carcasses are expensive, difficult to keep, have been processed enough to lack the same look and feel of live tissue, and animal anatomy is not analogous to human anatomy. These issues greatly limit the opportunities for practice and training.

For example, Fergal Kerins, Gregory Allan Whitton, Joshua Lee Richmond, and Timotheus Anton Gmeiner disclose Anatomical Simulators Produced Using 3D Printing in U.S. Pat. Appl. No. 20170291359A1. The 20170291359A1 application describes the production of an anatomical simulator using three-dimensional printing through the creation of molds. The 20170291359A1 application lacks substantial biomimicry. The 20170291359A1 application discloses three dimensional printed parts dissolved to create a negative space wherein biomimetic materials are limited only to matrix material used to fill the space but are not three dimensionally printed. The described methods and products lack modularity and processes for training.

Donald Russell Peterson, Simon Kudernatsch, Tulio Alberto Valdez disclose what they call a Modular Surgical Simulation Trainer and Methods of Use in U.S. Pat. Appl. No. 20170169733A1/CN104441664A. The 20170169733A1 Application describes a modular surgical simulator trainer that uses 3D printing to produce molds for casting dissectible anatomical surrogates from silicone elastomers, which are then placed in a housing to simulate various medical conditions. The housing is also 3D printed. The casted surrogates are designed to exhibit the properties of healthy tissue or pathological tissue, but they are not directly 3D printed. Furthermore, the 20170169733A1 Application does not use multi-material 3D printing, instead each anatomical part is composed of a single, homogenous silicone elastomer which would result in no variation in physical properties within an individual part. Finally, the 20170169733A1 Application does not incorporate an averaging algorithm in the design of its anatomical structures, but instead is designed to be patient specific, which fails to account for unique features present in an individual's anatomy and may skew a user's expectation of what normal anatomy is.

Matthew M. Dedmon, Neal P. Dillon, Patrick S. Wellborn, Robert F. Labadie, and Alejandro Rivas disclose Systems and Methods for Otologic Surgical Skills Training in U.S. Pat. Appl. No. 20180315348A1, which provides for a modular system with removable/attachable parts such as a housing and a "simulated ear canal port," but it teaches away from printing other anatomical simulations. For example, the 20180315348A1 Application is for simulating the working conditions for otologic surgical operations but does not always fully mimic actual human anatomy in appearance, structure, or biomechanical behavior. Instead, anatomical structures are only present in the training system if the appropriate "working port" is attached. The 20180315348A1 Application can swap between working ports, which can contain various exercises to improve instrument control and operative skills. The 20180315348A1 Application can possibly be 3D printed, however there is no indication of 3D printing with multiple materials that are mechanically interlocked. Furthermore, the 20180315348A1 Application lacks an averaging algorithm for the design of the surgical simulators, thus possibly skewing a trainee's sense of what is average or normal in anatomy. The 20180315348A1 Application is also limited in scope to otologic procedures.

马学晓 discloses Spinal Operative Method with Integration of Computer Simulation and 3D Printing in CN104441664A. The CN104441664A Application method uses CT scanning and MIMICS (a software by Materialise) to create a three-dimensional model of a patient's spine on a computer. The model displays "conditions of lesions" and surrounding tissue. Emphasis is placed on using the virtual model to determine an operative approach and provide for a virtual operation on the three-dimensional model, but the model is not printed until after the virtual operation. The three dimensionally printed model is used to "verify feasibility" of the virtual surgery on the computer. It neither provides for the use of biofidelic materials nor the modularity of the system of the inventions described herein.

Ronny Grunert, Mario Thalheim, and Dr. sc. Hum. Korb Werner disclose Simulation System for Surgical Procedures in Human and Veterinary Medicine in DE112006003722B4. The DE112006003722B4 Application is a non-modular system that focuses on using electric current in the physical models to train awareness for risk sensitive regions of a surgical operation. An object of this system is to train regarding tissue reactance to resin infiltration, not a surgical simulator that emulates actual tissue during an operation. The DE112006003722B4 Application relies upon electronic sensors in the model which are not required by the inventions described herein.

Inventors 黄广龙, 张点安, 彭俊祥, 石埕, 潘军, 殷延毅, 吴益萍, 邱晓瑜, and 漆松涛 disclose Full Simulation Neurosurgery Platform based on 3D-Printing and Cyclic Breath Reconstruction in CN106228883A. The CN106228883A Patent is a neurosurgery platform that has a modular factor; removable brain components including blood vessels, nerves, and brain tissue models. It emphasizes breathing recreation in surgical simulation via liquid circulation in the system and blood flow recreation such as pulsating vessels. It does not disclose the methods and inventions herein described.

Cameron Piron, Joshua Richmond, William Lau, and Sheryl Thingvold disclose Surgical Training and Imaging Brain Phantom in in U.S. Pat. Appl. No. 20160155364A1. The 20160155364A1 Application focuses models of a mammalian head and brain. The 20160155364A1 Application is not applicable to the generalizability of other anatomical structures. The 20160155364A1 Application describes three dimensional printed molds, not of the phantoms themselves or generation of the molds in a manner consistent with the inventions herein described.

Inventors 汤润, 朱海涛, 江洋, and 孙晓青 disclose 3D Kidney Model Printing Method for Kidney Stone Surgical Simulation Training in CN105105847A. The CN105105847A Application uses CT scanning and MIMICS software to make virtual 3D reconstruction of kidneys. The CN105105847A Applcaition does not suggest or disclose the applications and use of three dimensionally printed or molded biofidelic materials and/or modularity described herein.

The Fractured FX and the Simulator Program at the Boston Children's Hospital (SIMPeds) uses FX makeup to make simulators appear more real. It takes a different approach than described herein.

Stratasys is a three-dimensional printing company whose three-dimensional printers are in use for a range of medical three dimensional printing, including trainers and simulators. Components for the inventions described here can be made using the Stratasys J750 Digital Anatomy 3D Printer, along other kinds of three-dimensional printers. Stratasys notes that three dimensional printed models can mimic a range of tissues more realistically than processed cadavers, which no longer retain the feeling of live tissue. Existing methods have very limited diversity of material properties. For instance, Stratasys has two materials for anatomical printing called TissueMatrix™ and BoneMatrix™, purported to simulate heart tissue and bone tissue respectively. However, while the J750 Digital Anatomy 3D Printer and other similar PolyJet technology printers from Stratasys are capable of multi-material 3D printing, it is crucial to note that the multiple materials used in Stratasys PolyJet printers are all curable liquid photopolymers, which are similar materials that can be blended together and bonded chemically. The method of multi-material printing from Stratasys is significantly different from the methods of multi-material printing described herein, which takes advantage of layer-by-layer extrusion to create volumes of 3D geometries that overlap in such a way as to mechanically interlock dissimilar materials.

GTSimulators produces three-dimensional printed anatomy models and medical simulators, but those are separate products. GTSimulators' three-dimensional printed anatomy models are not designed for surgical practice, and GTSimulators' medical simulators are not designed for surgical practice either, nor are the simulators three dimensionally printed.

University of Rochester's Simulated Inanimate Model for a Physical Learning Experience (SIMPLE). The project uses hydrogel to create three-dimensionally printed organs, with materials used to mimic live tissue.

https://www.urmc.rochester.edu/news/story/4668/creating-the-model-human-to-practice-surgery.aspx BIOMODEX, based in France has the " . . . vision . . . to revolutionize preoperative planning resulting in safer surgical procedures and improved patient outcomes", suggesting use than training. The founders are Thomas Marchand and Sidarth Radjou. There is no clear mention of modularity and customization, but BIOMODEX uses CT/MRI segmentation, high fidelity models using biofidelic materials, and models being dissectible for practicing surgical techniques. Yet the service specifically designed for preoperative preparations catered to specific patients—not generalized and/or computer selected trainers and anatomical parts for general training. In addition, inventors Frederic Champ, Samuel Orru, and Celement Jubert of BIOMODEX disclose Multi-Material Three-Dimensional Printed Portion of a Heart in WO 2021137173A1, which describes a mimicked portion of a heart that is 3D-printed using multiple materials, specifically photopolymerized Acrylate-Based PEG Hydrogels. The portion of the heart in question is printed using multiple materials by sandwiching a one material between layers of another material. There is also a plurality of polygons composed of the first material, and "each said polygon defining an interior portion filled with a second material different from the first material". Although this multi-material printing technique of the WO 2021137173A1 Application may appear similar to the method of printing interlocking volumes described herein, the WO 2021137173A1 Application technique is intended to only change the physical and mechanical properties of the specified heart portion, rather than to connect multiple anatomical structures of dissimilar materials together. Furthermore, the WO 2021137173A1 Application is limited in scope to using acrylate photopolymerized resin and hydrogels with a specified Young's Modulus of 0.3 and 7 MPa.

MEDICAL IP, based in South Korea, is a proclaimed "world leader in medical imaging and its 3D visualization application," but also offers a 3D printing service called Anatdel, which includes the production of patient specific models and training simulators. There is no clear indication of modularity and customization, and MEDICAL IP seems to focus on patient specific replication, but MEDICAL IP does appear to directly print its models using biofidelic materials with the intention of dissection for practicing surgical techniques. However, the service seems to indicate that the models are printed using only one kind of printing technology.

Zainal Ariff Bin Abdul Rahman, Vickneswaran A/L Mathaneswaran, Alwin Kumar Rathinam, Yuwaraj Kumar A/L Balakrishnan, and Su Tung Tan disclose Method for Manufacturing a Three-Dimensional Anatomical Structure in U.S. Pat. Appl. No. 2016/0287339A1, which describes a method for manufacturing a three-dimensional anatomical structure by using "grey values" from a plurality of medical images for segmentation. Segmentation is a standard method of creating three-dimensional objects from medical images. The 2016/0287339A1 Application method also has an embodiment that uses the Marching Cube algorithm. However, even though the Marching Cube algorithm is used by a possible embodiment of the 2016/0287339A1 Application, the algorithm itself is commonly used in rendering 3D data. Therefore, the distinctive use of the Marching Cube algorithm described herein is unique due to its being part of a larger, novel averaging algorithm for anatomical design.

Andres Bernal discloses Method for Fabricating Simulated Tissue Structures by Means of Multi Material 3D Printing in U.S. patent Ser. No. 10/290,236B2, which describes a method for creating a synthetic eye model. The 2016/0287339A1 Application model is manufactured by assembling modular sub-components that can be 3D printed. Both my invention and 2016/0287339A1 Application start by establishing target anatomical structures and auxiliary anatomical structures, segmenting said structures, and then modifying the 3D models for 3D printing. However, the method of multi-material 3D printing referred to in the 2016/0287339A1 Application is to blend multiple, curable liquid photopolymer together into a single, homogenous material, akin to how alloys of a metal are made, per substructure. Therefore, the 2016/0287339A1 Application multi-material 3D printing method is simply the direct application of certain commercial 3D printers. In fact, 3D printing may not even be necessary for the 2016/0287339A1 Application given that each sub-component is made of a single material and the final anatomical model is assembled after printing. It can be argued that molding each sub-component and then assembling will result in the same result. This is in contrast with the invention disclosed herein, where 3D-printing is necessary for the novel interlocking technique as a means of combining anatomical structures of dissimilar materials together. There is also no averaging algorithm indicated in 2016/0287339A1 Application, which is a component to the invention disclosed herein.

Niall Haslam, Lorenzo Trojan, and Daniel Crawford disclose Method for Generating a 3D Physical Model of a Patient Specific Anatomic Feature from 2D Medical Images in U.S. patent application Ser. No. 11/138,790B2, which describes a procedure whereby 2D images are uploaded by an end-user via web application and a server will automatically process the images and use segmentation to produce patient specific 3D printable models in a 1:1 scale. While both of U.S. Ser. No. 11/138,790B2 and my invention use the common industry practice of segmenting 2D medical images to design 3D anatomical models that mimic biological structures, the methodology of my invention distinctly uses an averaging algorithm to remove patient-specific features in the anatomical models. Furthermore, the physical production of the anatomical models described in U.S. Ser. No. 11/138,790B2 is not listed in its claims. This is yet another differentiation from my invention, which does include multi-material printing as a means of physically producing biofidelic anatomical models after the design process.

Vera Seitz, and Hannah Riedle disclose Anatomical Silicone Models and Additive Manufacturing Thereof in U.S. Pat. Appl. No. 20200316850A1, which relates to a method of additive production using 3D printers to produce anatomical models. The listed steps described in US20200316850A1 involve a "layer-by-layer application of printing compounds in the form of drops," which the printing compounds are then crosslinked by electromagnetic radiation. These steps are repeated until the anatomical model has been completely built. Notably, these steps of US20200316850A1 are not a new method of 3D printing, but rather a description of PolyJet 3D printing and Multijet 3D printing, which there are several commercially available 3D printers that utilize these technologies. The claimed methods of US20200316850A1 are general and describe common, basic procedures of segmentation, 3D model design and additive manufacturing/3D printing. What is specific to US20200316850A1 is the use of cross linkable silicone rubber compositions as a 3D printing material for anatomical mimicry. Significantly, US20200316850A1 lacks both an averaging algorithm in its process of designing 3D anatomical models and multi-material printing using interlocking volumes to mechanically join multiple anatomical bodies of dissimilar materials together.

Cherkassiky et al: published a study titled Patient-specific 3D Models Aid Planning for Triplane Proximal Femoral Osteotomy in Slipped Capital Femoral Epiphysis, which studied the effects of 3D-printed models for surgical planning. The study used patient-specific models and found that surgical time was reduced with the use of the model compared to surgical operations that proceeded without the 3D printed models. This publication by Cherkassiky et al. differs from my invention because the 3D models produced in the study are patient specific, do not indicate multi-material printing and do not indicate that the anatomical structures around the model of focus are produced. Furthermore, this study by Cherkassiky et al. also focuses on case-specific preoperative rehearsal/planning rather than standardized training.

Rose et al. Published a study titled Multi-Material 3D Models for Temporal Bone Surgical Simulation, which studied the effects of using 3D printed temporal bone models for training. The models are printed in multiple colors and materials using PolyJet technology, which is the commercial function of the printer used: the Object350 Connex from Stratasys. Crucially, this means that the method of multi-material 3D printing described in this study differs from the method of the invention disclosed herein. The study emphasizes the use of biofidelic materials and the production of auxillary anatomical structures, which appears to benefit to surgical training. Therefore, this study by Rose et al. supports the need for the invention disclosed herein and its novel improvements, such as the averaging algorithm to better design exemplar models for training.

Inventors 杨越雄, 陈强, 胡红霞, and 张晓峰 disclose a Method for Manufacturing Soft Tissue Pathological Model by means of New Material 3D Printing in CN105427727A, which relates to the 3D printing of soft tissue models, including anatomy of focus and its surrounding tissues. The anatomical models are designed using DICOM data, which is a common industry practice. However, the method of printing described in CN105427727A is unique in that it uses red, green, and blue silca gels as printing materials. This printing methodology is different from that of my invention. It can also be stated that methods described in CN105427727A do not indicate multi-material printing because the silca gels used differ from each other only in color, with no indication of deviation by chemical formulation.

BRIEF SUMMARY OF THE INVENTION

The invention is a design and manufacturing process/procedure to create a variety of modular surgical simulators. These surgical simulators are artificial replications of one or more surgical sites, which include relevant anatomy, and mimic tissue characteristics/behaviors. The process begins with acquiring CT and MRI scans of a surgical site of interest, and using a process called segmentation to create three-dimensional printing models of the surgical site's anatomy, in different formats called STLs, OBJ, 3MF, AMF, etc. and/or other equivalents, from those scans. The STLs are averaged together by patient profile to make a representative exemplar, and then three dimensionally printed in appropriate biofidelic materials using several kinds of three-dimensional printers to create artificial replications of anatomy of interest. The three-dimensional printed anatomy models are then assembled together with spatial accuracy to create a modular, dissectible surgical trainer for the surgery to be practiced.

This invention produces anatomically and spatially accurate surgical sites using biofidelic materials to best mimic a human body to practice on, with full customization options to mimic variables that one may come across and desire experience in handling.

Prior art tends not to use direct three-dimensional printing in the manufacturing of anatomical parts, but instead chooses to make molds for casting. The issue is that molds are static and cannot be modified to mimic variables of interest in surgery. They lack customization in manufacturing unless another mold with appropriate adjustment is made. The invention enables the simple adjustment of the STLs and 3D printing parameters to desired characteristics and settings for customization. For instance, the invention enables modification of the model (what is being made) and the printing parameters known as slicing (i.e. how the printer will make the model).

Furthermore, conventional molds are limited to use of only one material, which limits the component's properties. However, human anatomical structures are dynamic and heterogenous, with different properties at different locations of the same structure. For example, a single bone is comprised of different types of tissues, including cortical bone, cancellous bone, and marrow; all with different properties and behaviors which demand multiple materials to fully replicate. This can only be done with additive manufacturing that is three-dimensional printing. The inventions disclosed herein allow for multi-material components including within a single anatomical body. Thus, multi-material can refer to a single object, not just an assembled collection of homogenous parts that are each themselves a different material.

To create objects featuring fully integrated multiple materials, without necessitating post-printing assembly, fastening, or adhesions, a novel method of multi-material 3D-printing has been developed. Multi-material 3D printing has been practiced in all branches of 3D printing technologies but has traditionally been limited to materials that are chemically compatible for fusing during the printing process. In this invention, a novel method of 3D printing design and slicing has allowed the circumvention of limited material compatibility. The described method involves the Boolean intersection of components that are intended to be made from different materials. The intersecting volume can then be modified to take on a variety of lattice structures or equivalents as to facilitate a three dimensional interlace of the different materials. The result is a primarily mechanical connection between the different materials within or between 3D printed objects that is not reliant on chemical bonding, adhesives, mechanical fixations, or other methods of assembly. This method of interlacing multiple materials negates the need for post-printing assembly, can be used for multiple materials that are not traditionally suited for chemical bonding, can be easily modified to change mechanical properties and other features of the intersecting volume to desire, and can be used in all 3D printing technologies, including but not limited to FFF or Material Jetting with single or multiple extruders. Lattices and 3D weaving are not limited in the cross-sectional shapes used in composing the structures. Further applications of this technique can be used in 4D printing, such as when trying to create objects that change shape only in certain sections, while leaving other sections unaffected in the presence of a trigger. The technique can also be used for creation of other products such as medical devices that desire an integrated union of multiple materials within or between components.

Molds also create homogenous, isotropic parts, which human anatomy is not. For example, muscles have striations, meaning that the fibers run alongside each other. Three-dimensional printing can lay material down in the same fashion, by extruding material in the form of lines running alongside each other to simulate the striations. Molds cannot do so because they are cast and solidified as a homogenous part. The inventor's process disclosed herein allows for structurally accurate, heterogenous anatomical components.

While there are dissectible models for surgical training on the market, many are not modular, customizable, reusable, biofidelic, or anatomically accurate/reflective to specific biological profiles/demographics, as they are sourced from specific individuals or cadavers. Such individual specific models do not facilitate generalizability of skills to a broader patient population that do not share said individual model's features.

There are also cases of three-dimensional printing anatomy with biofidelic materials for pre-op by surgeons to plan and practice a specific operation for a specific patient. However, such cases are almost always limited to a few anatomical structures or organs of interest, and do not include surrounding tissues and structures that will be present during surgical operation. It does not recreate a full surgical site, which the inventor's process does. Also, existing processes and models lack spatial fidelity to true anatomy which is better created through my invention.

Although the invention is illustrated and described herein as embodied in a method, system and device for generating anatomical parts, the invention is not limited to the details shown because various modifications and structural changes may be made without departing from the invention and the equivalents of the claims. However, the construction and method of operation of the invention together with additional objects and advantages thereof will be best understood from the following description of specific embodiments when read in connection with the accompanying drawings.

Figure 1:
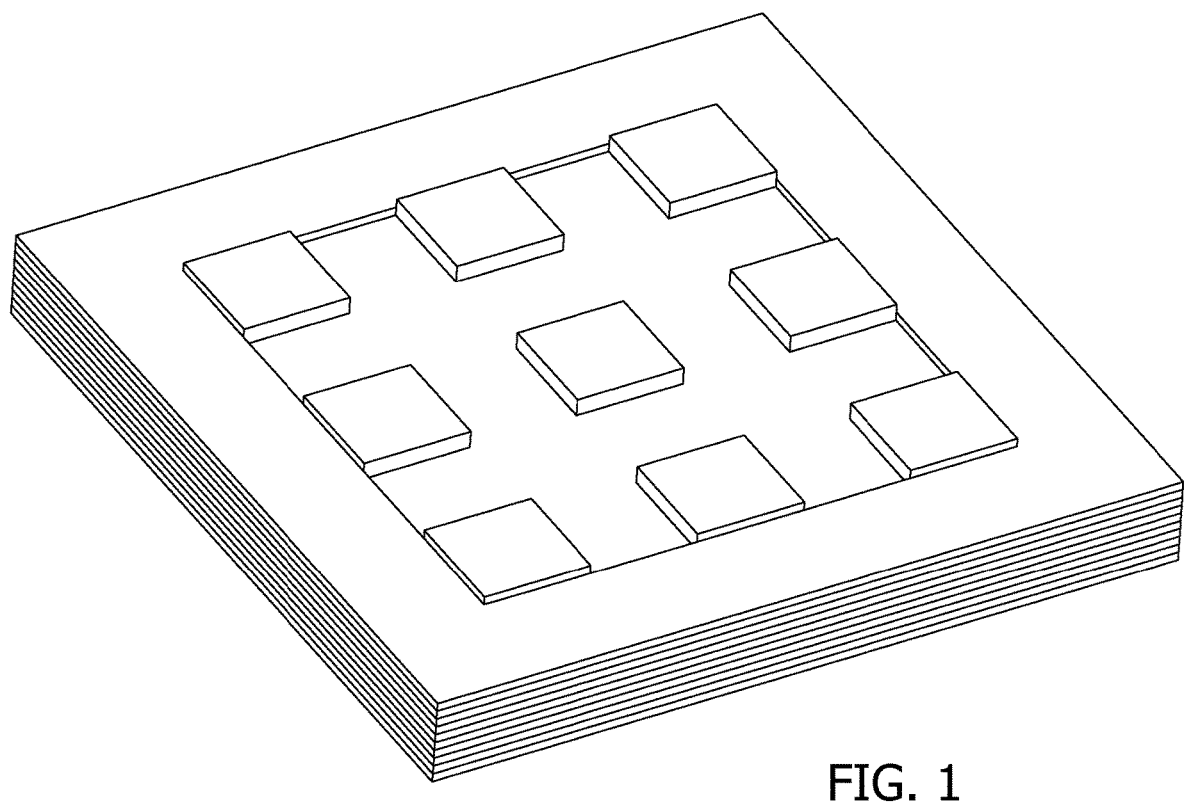
FIG. 1 illustrates an example body of interlocking lattices comprised of complimentary lattice patterns, each of which corresponds to a distinct body and/or material. The body of FIG. 1 is not limited to any shape or form, as the complementing lattices can be adopted to any shape or form, of any volume.

Each lattice body, when separated, cannot be assembled into the combined body exemplified in FIG. 1.

Figure 3:
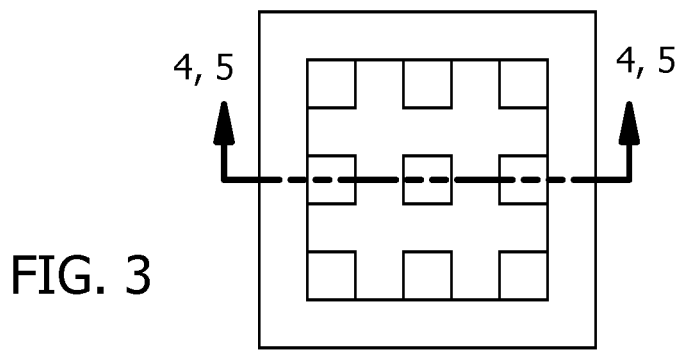

FIG. 3 is a plan view of the example body of combined interlocking lattices illustrated by FIG. 1.

Figure 4:
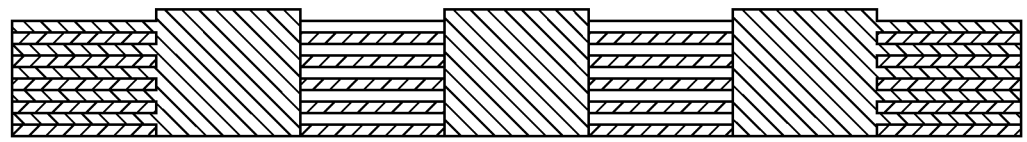

FIG. 4 illustrates a cross sectional view of the example body of combined interlocking lattices illustrated in FIG. 3, taken along line 4, 5.

Figure 5:
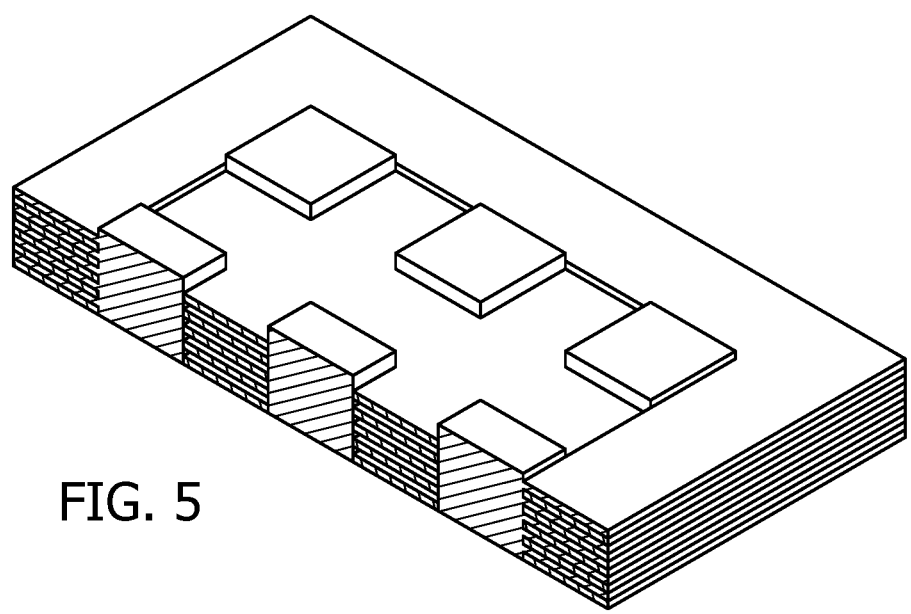

FIG. 5 is perspective view broken away of the combined lattice bodies illustrated in FIG. 4.

Figure 2:
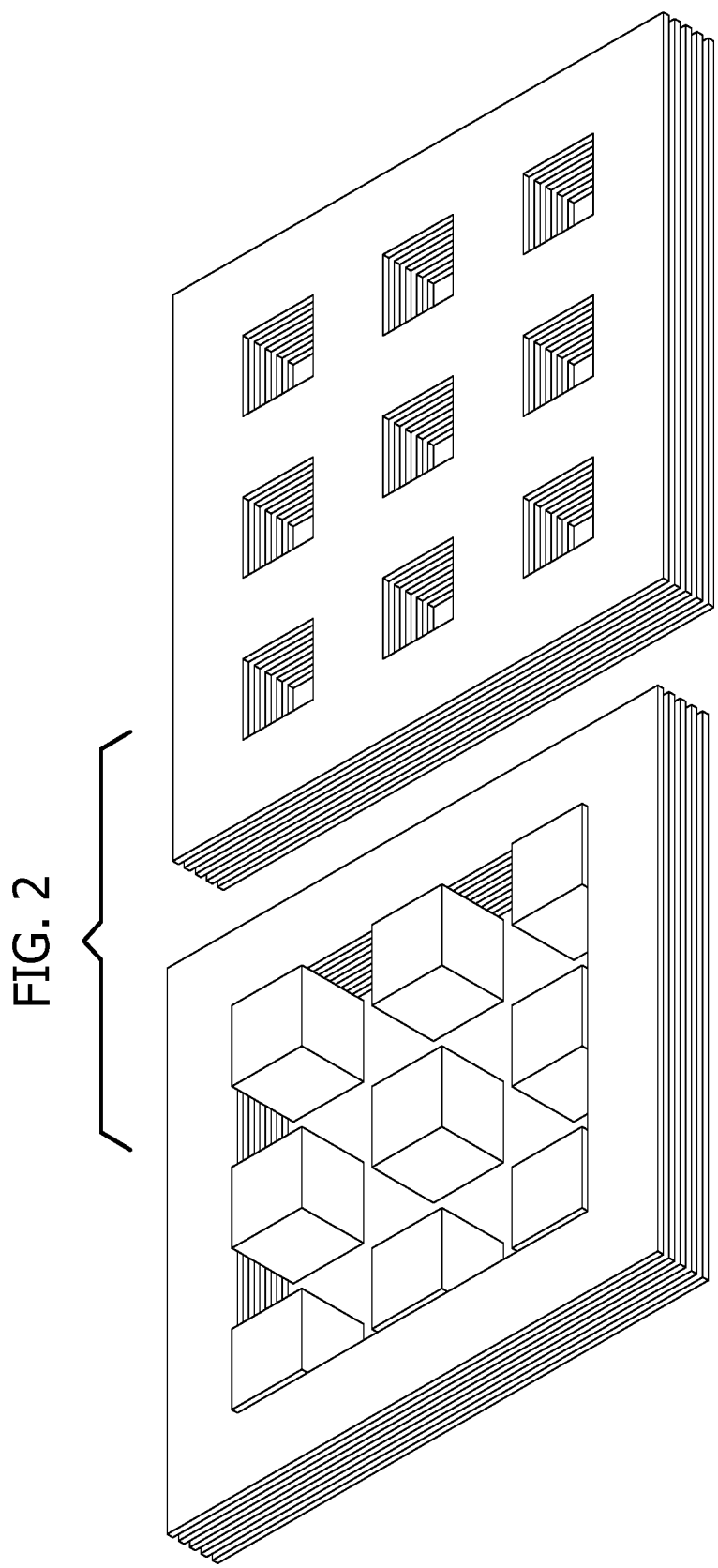
FIG. 2 illustrates the example body of interlocking lattices of FIG. 1 separated into two distinct bodies and/or materials comprised of complimentary lattices. Each distinct lattice body in FIG. 2 is not limited to any specific shape or form, and can be adopted to any shape or form, of any volume.
Figure 6:
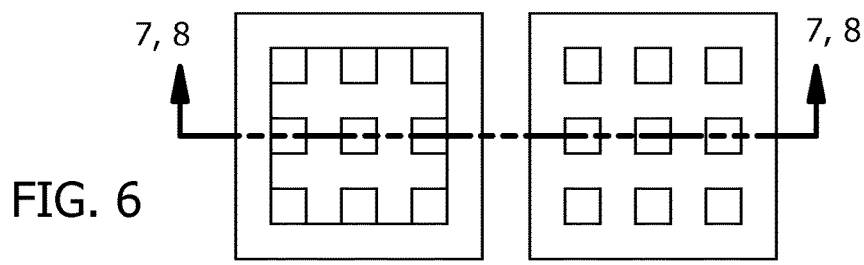

FIG. 6 is a plan view of the two separate, distinct lattice bodies illustrated in FIG. 2.

Figure 7:
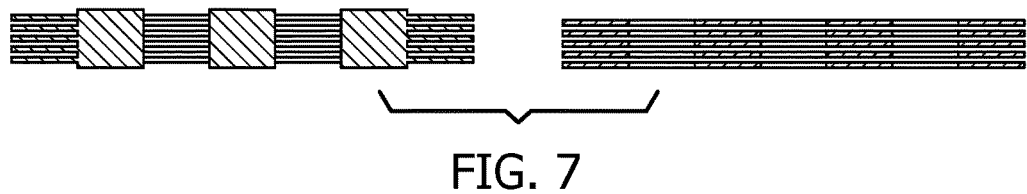

FIG. 7 illustrates a cross section view of the separate, distinct lattice bodies, taken along line 7, 8 in FIG. 6.

Figure 8:
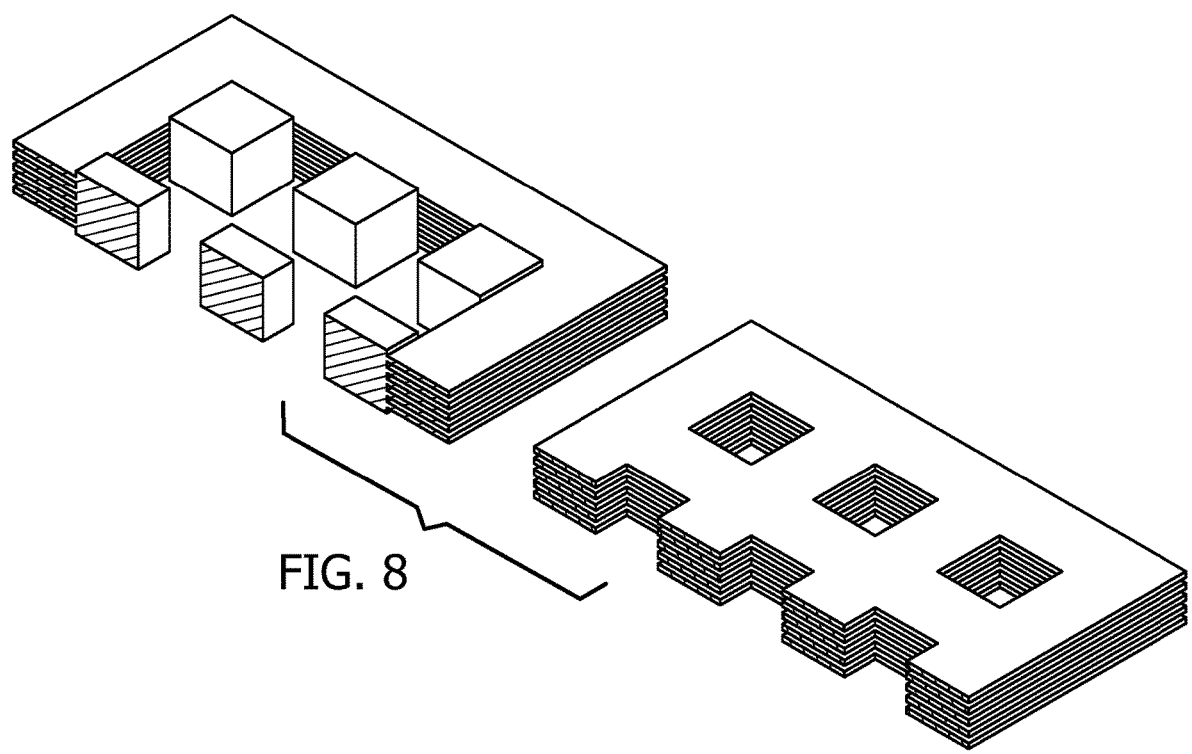

FIG. 8 is a perspective view broken away of the separate, distinct lattice bodies illustrated in FIG. 7.

Figure 9:
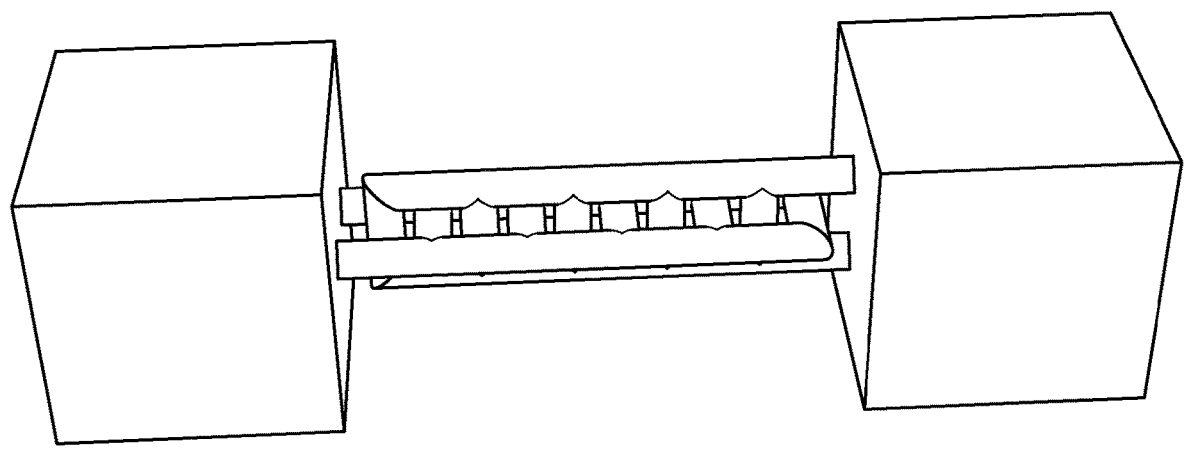

FIG. 9 illustrates an example of an integrated mechanical joint to interlock different bodies and/or materials, represented by two distinct bodies that are combined using mechanical linkage, akin to a chain with alternating links. The integrated joint exemplified in FIG. 9 is not limited in form, size, or number of linkages involved.

Figure 10:
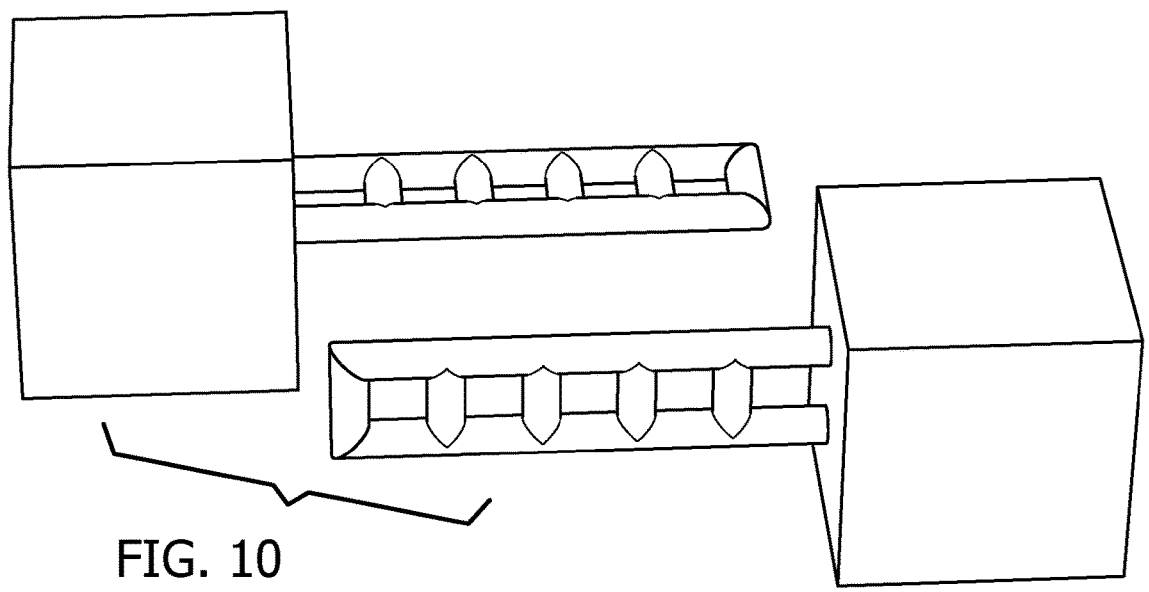

FIG. 10 illustrates the two distinct bodies and/or materials illustrated in FIG. 9 as separate bodies that are not interlocked using a mechanical joint. The two distinct bodies are unable to be combined together using integrated mechanical linkage as illustrated in FIG. 9.

Figure 11:
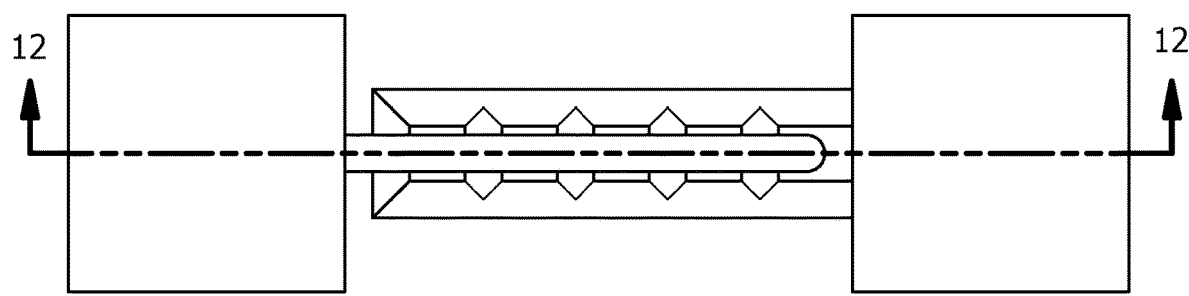

FIG. 11 is a plan view of the interlocked bodies and/or materials illustrated in FIG. 9.

Figure 12:
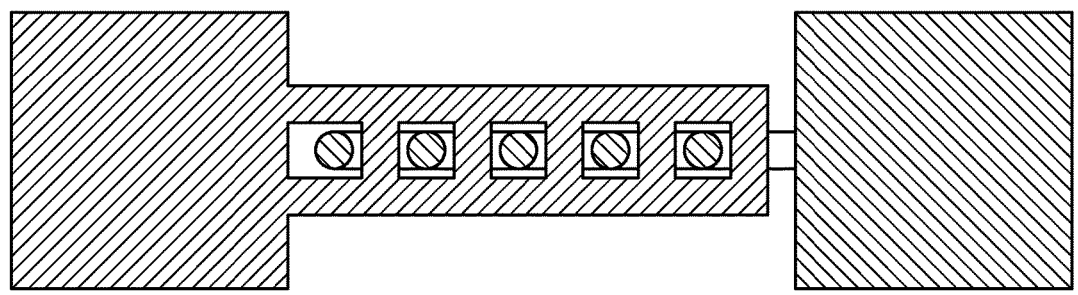

FIG. 12 illustrates a cross section view of the distinct bodies and/or materials illustrated in FIG. 11, taken along line 12.

Figure 13:
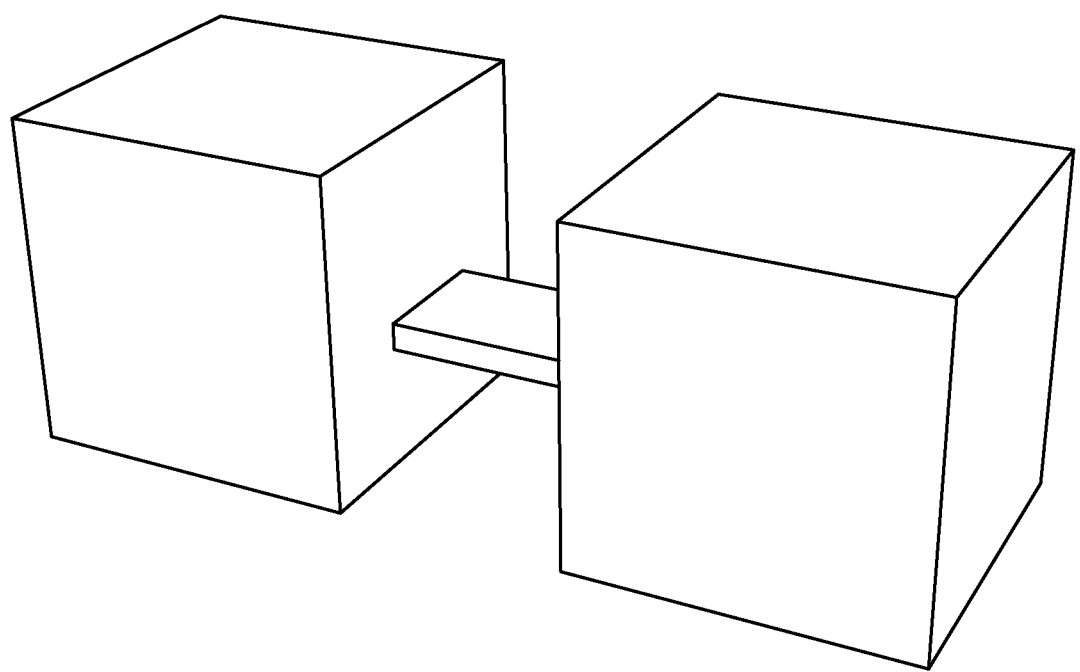

FIG. 13 illustrates two distinct bodies and/or materials interlocked together using an integrated mechanical joint in the form of a loop, akin to an eye bolt.

Figure 14:
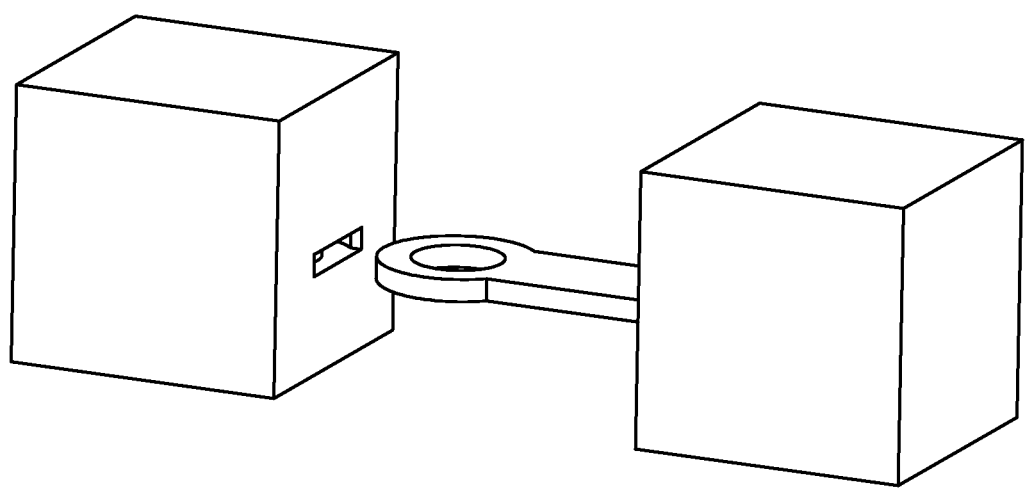

FIG. 14 illustrates the two bodies and/or materials illustrated in FIG. 13 as separated. When separated, the two bodies are unable to be interlocked using integrated mechanical joints.

Figure 15:
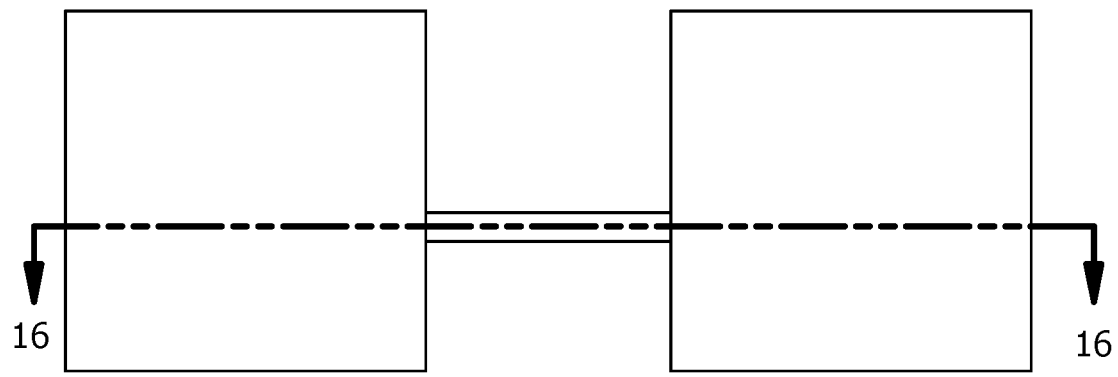

FIG. 15 illustrates a side view of the two bodies and/or materials illustrated in FIG. 13.

Figure 16:
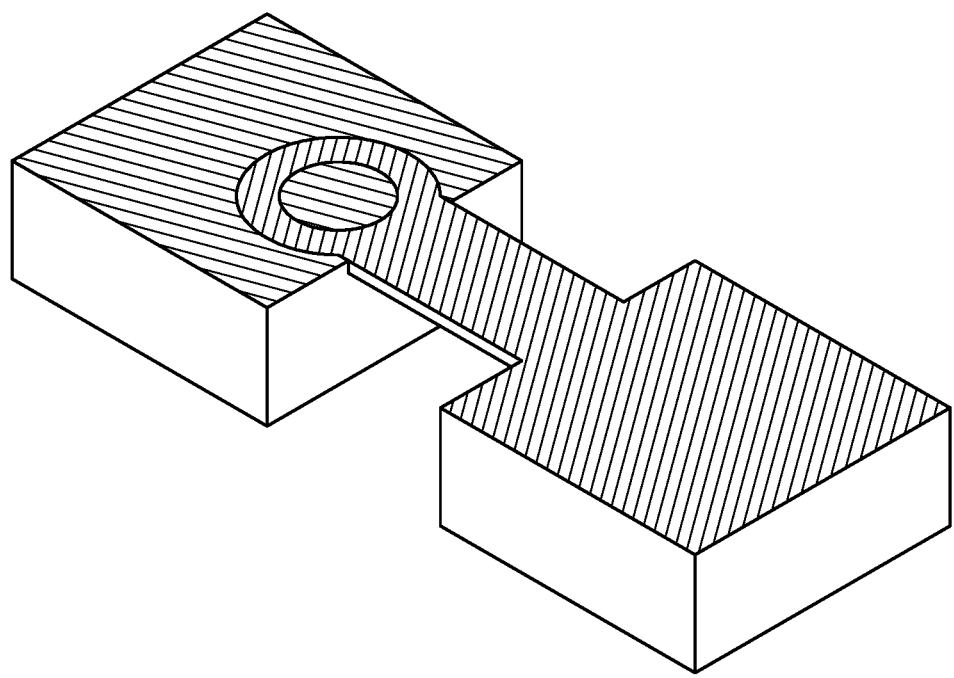

FIG. 16 illustrates a cross section, perspective view of the two distinct, interlocked bodies and/or materials illustrated in FIG. 15, taken along line 16.

Figure 17:
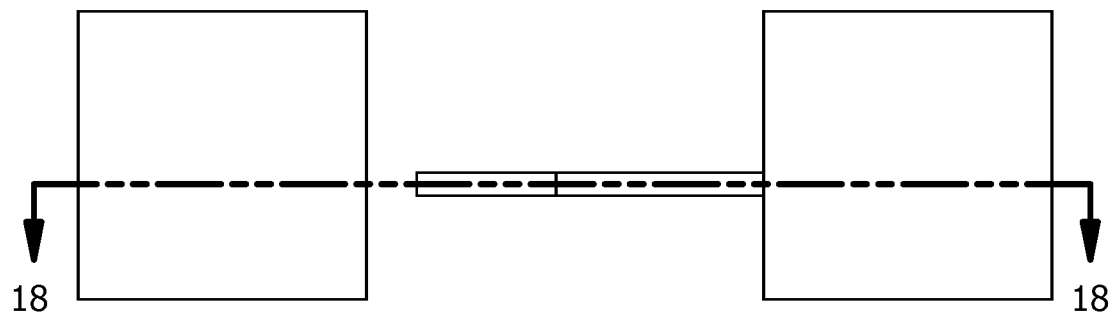

FIG. 17 illustrates a side view of the two separated bodies and/or materials illustrated in FIG. 14.

Figure 18:
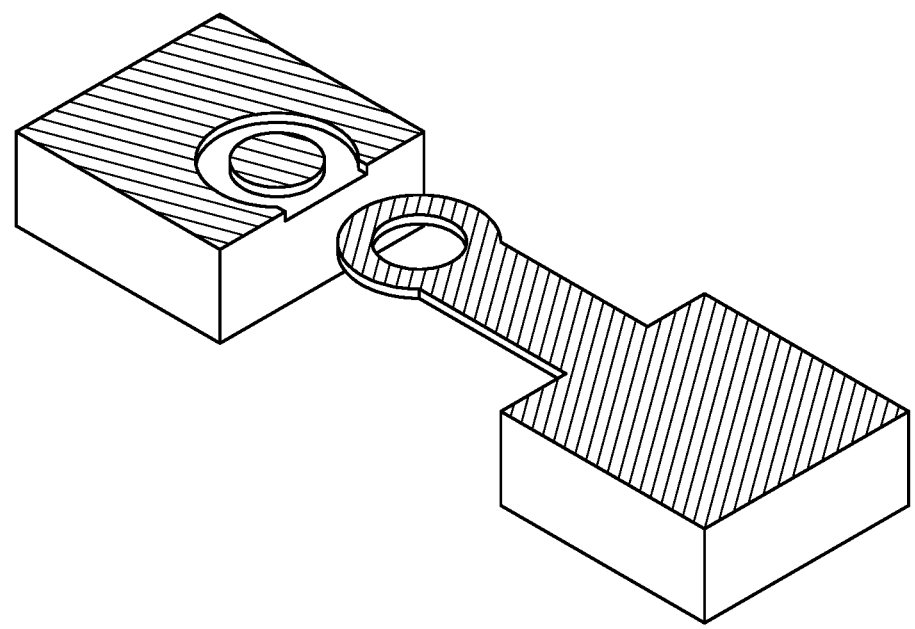

FIG. 18 illustrates a cross section, perspective view of the two distinct, separated bodies and/or materials illustrated in FIG. 17, taken along line 18.

FIG. 19 illustrates two distinct bodies and/or materials interlocked using integrated mechanical joints in the form of curved shafts, akin to noncontinuous suturing.

FIG. 20 illustrates the two bodies and/or materials of FIG. 19 as separated. When separated, the two bodies and/or materials are unable to be interlocked using integrated mechanical joints.

FIG. 21 is another perspective view of the two separated bodies and/or materials shown in FIG. 20.

Figure 22:
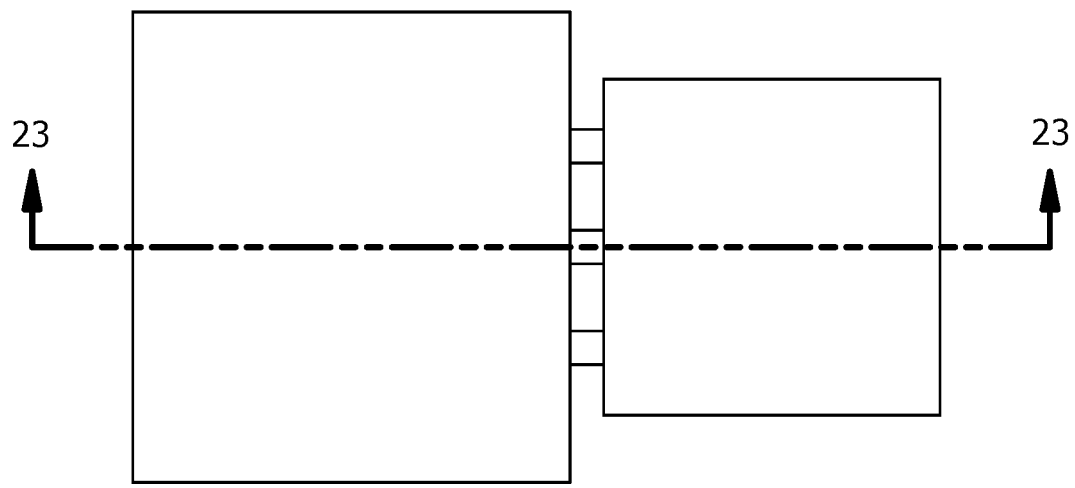

FIG. 22 is a plan view of the interlocked bodies and/or materials illustrated in FIG. 19

Figure 23:
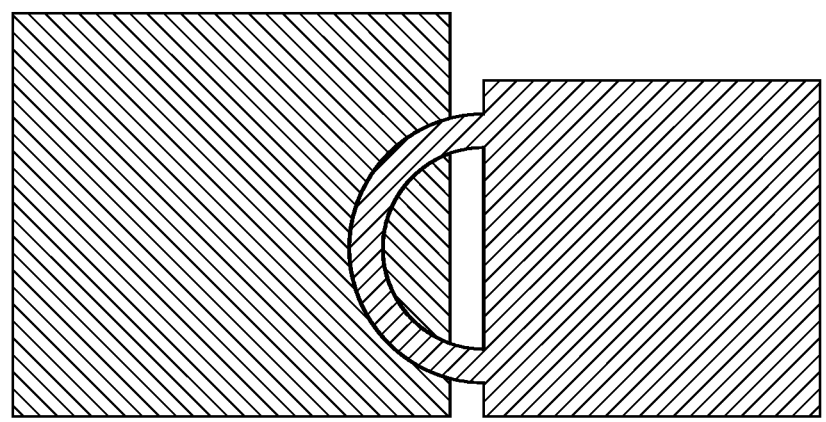

FIG. 23 is a sectional view of the interlocked bodies and/or materials illustrated in FIG. 22 taken along line 23.

Figure 24:
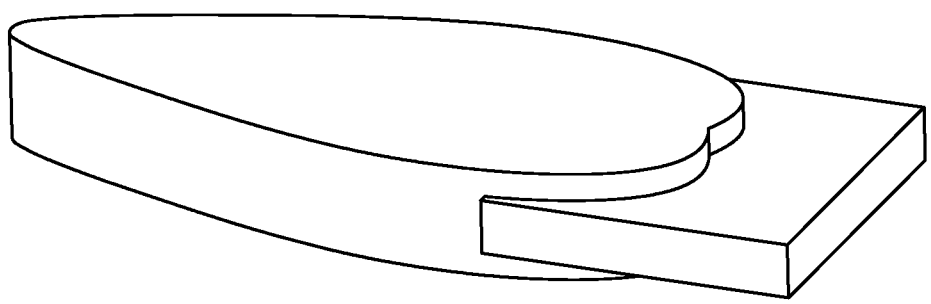

FIG. 24 illustrates two distinct bodies and/or materials interlocked together using integrated mechanical joints in the form of pin joints.

Figure 25:
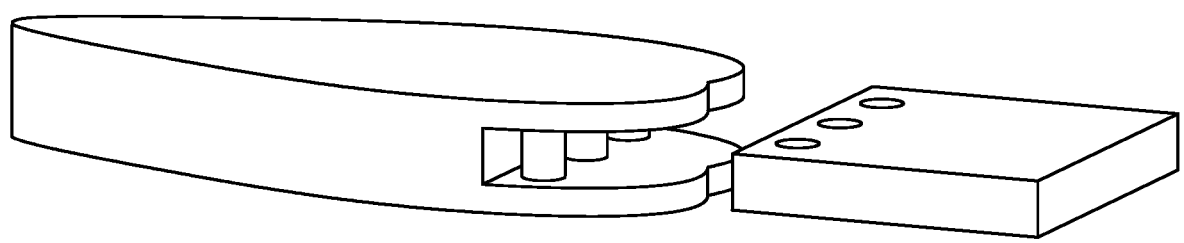

FIG. 25 illustrates the bodies and/or materials of FIG. 24 as separated. When separated, the two bodies are unable to be interlocked through integrated mechanical joints.

Figure 26:
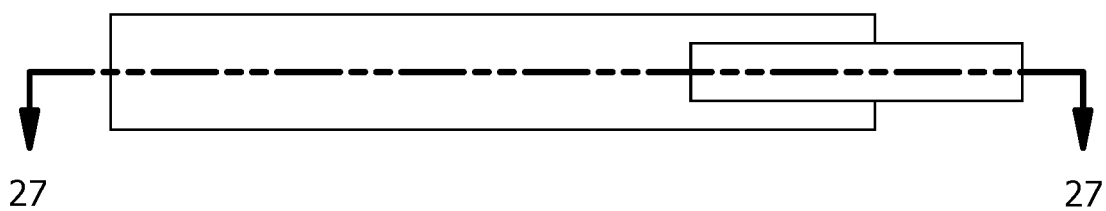

FIG. 26 illustrates the interlocked bodies and/or materials of FIG. 24 from a side view.

Figure 27:
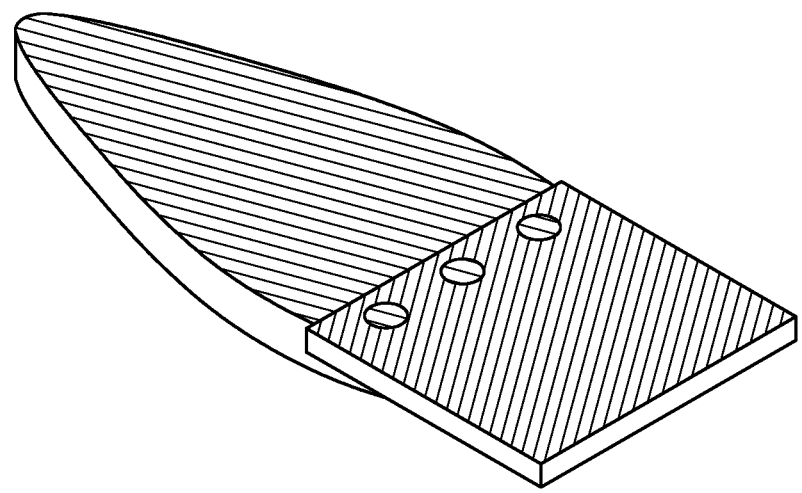

FIG. 27 is a perspective, cross section view of the interlocked bodies and/or materials of FIG. 26, taken along line 27.

Figure 28:
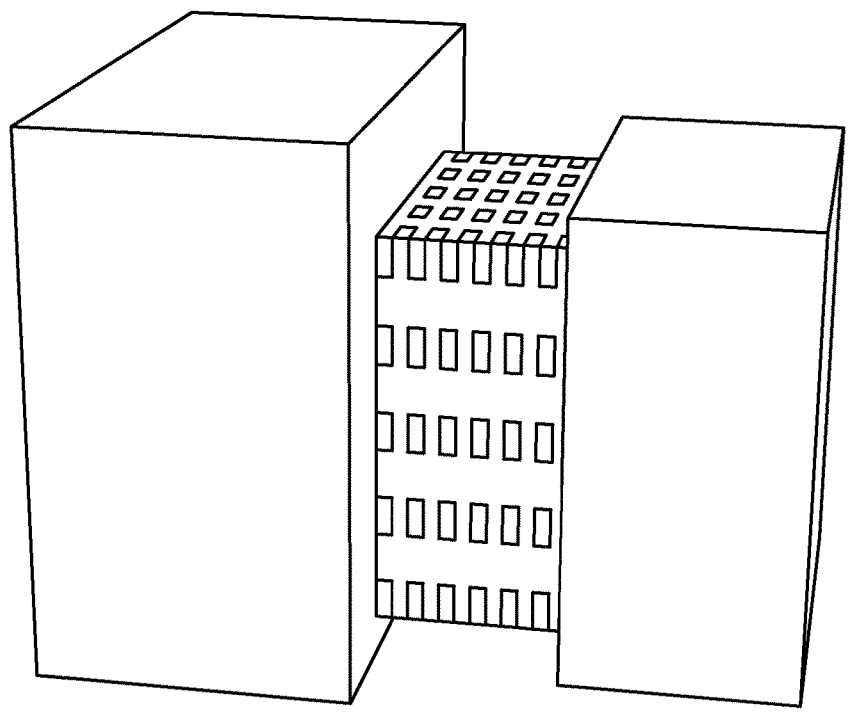

FIG. 28 illustrates two distinct bodies and/or materials combined using a shared volume of interlocking lattices. Each body and/or material's attached lattice fills in the empty space of the other body's lattice, thereby mechanically weaving them together in a three-dimensional joint.

Figure 29:
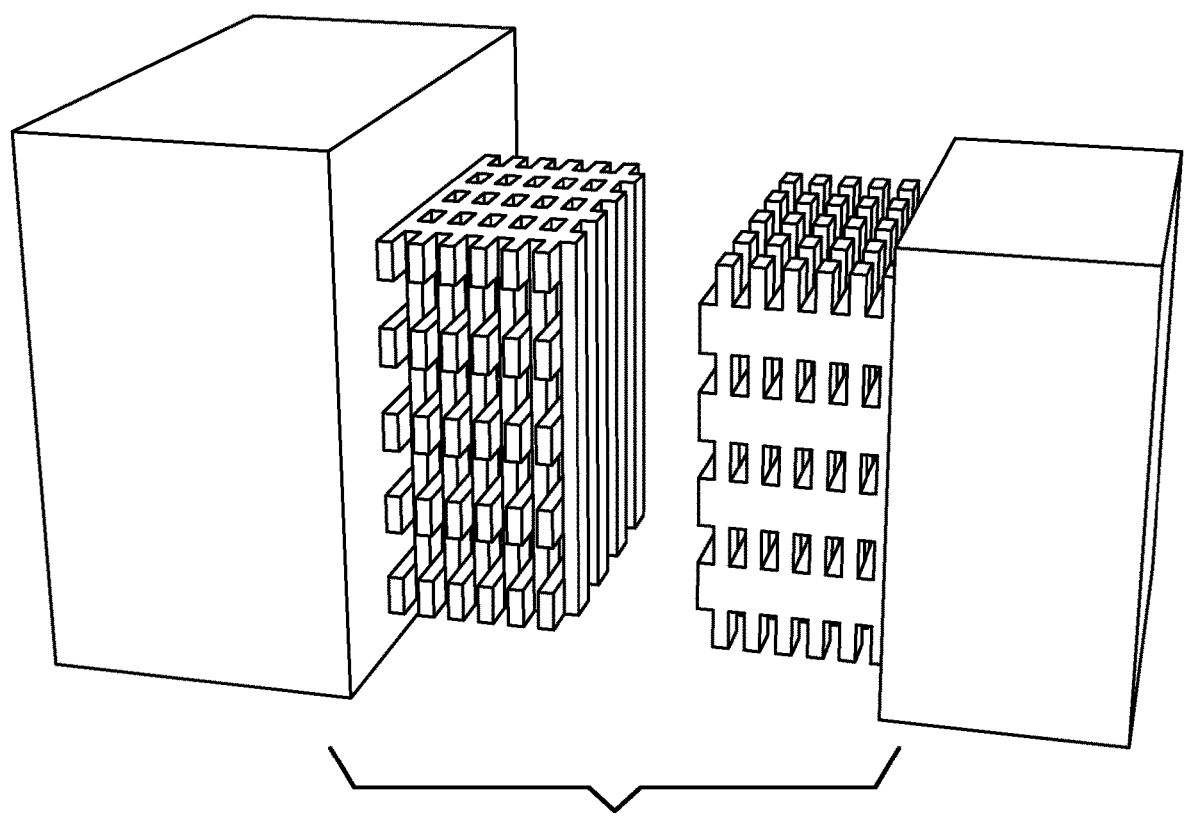

FIG. 29 illustrates the two distinct bodies and/or materials of FIG. 28 as separated. When the bodies and/or materials are separated, they are unable to be interlocked using integrated mechanical joints.

Figure 30:
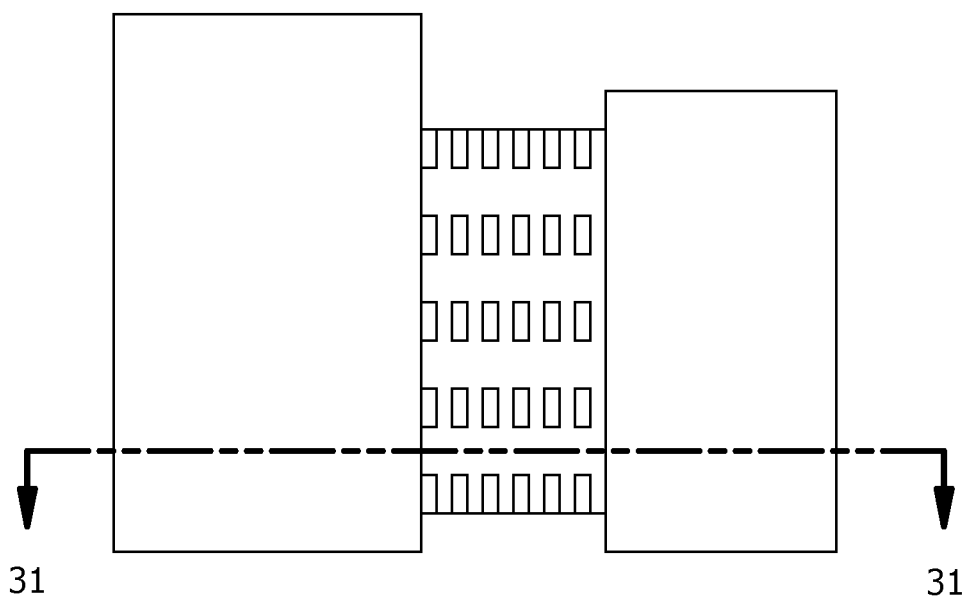

FIG. 30 is a side view of the two interlocked bodies and/or materials of FIG. 28.

Figure 31:
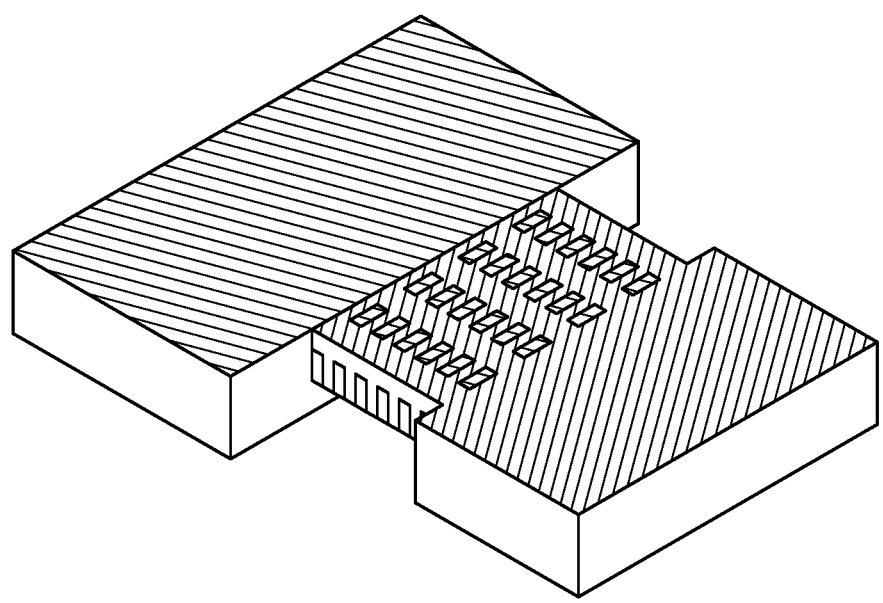

FIG. 31 is a perspective, cross section view of the two interlocked bodies and/or materials of FIG. 30, taken along line 31.

Figure 32:
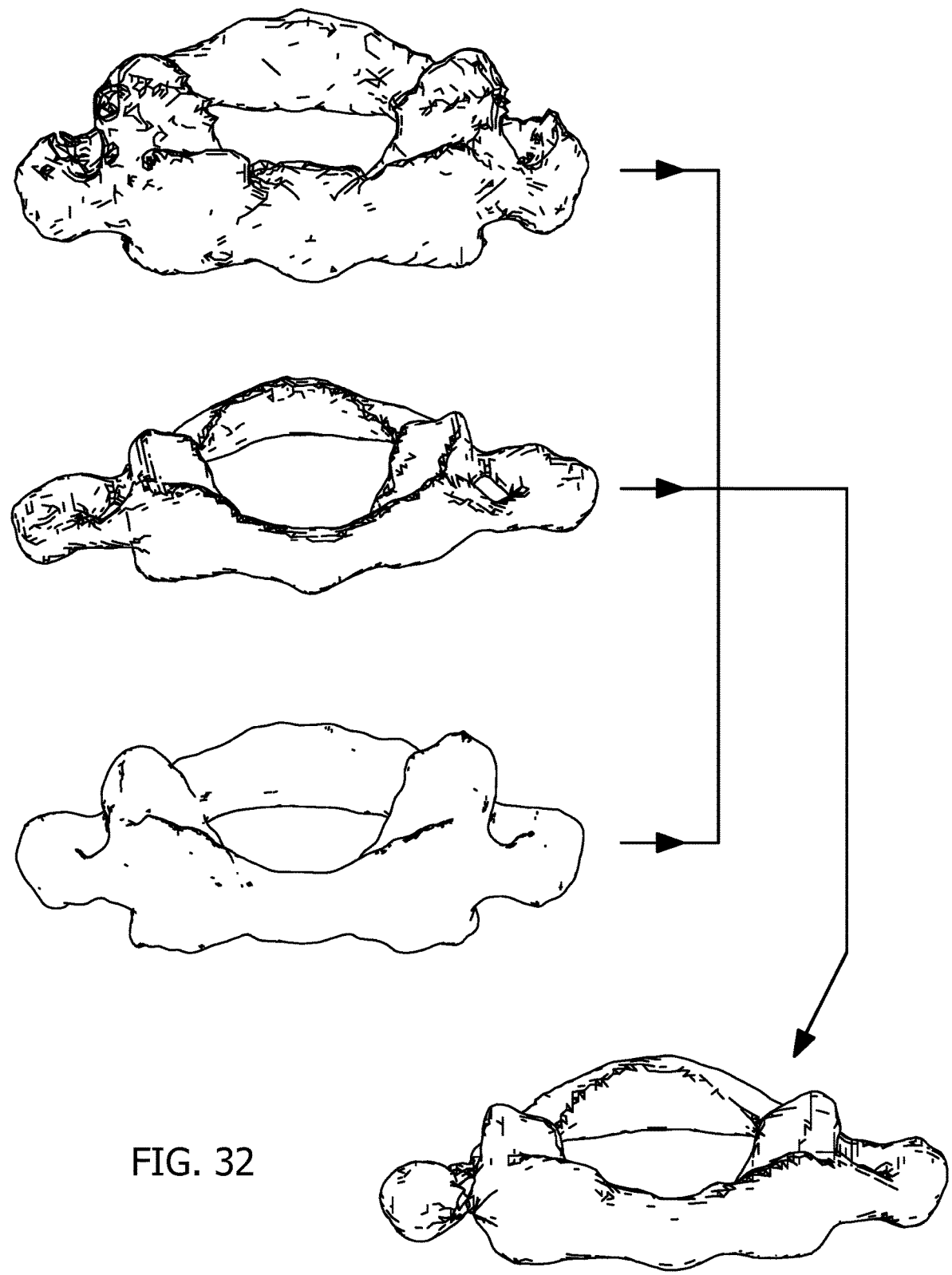

FIG. 32 illustrates three distinct C1 (atlas) vertebrae that are inputs in the algorithm that results in an exemplar model as the average resultant of the three original inputs.

Figure 33:
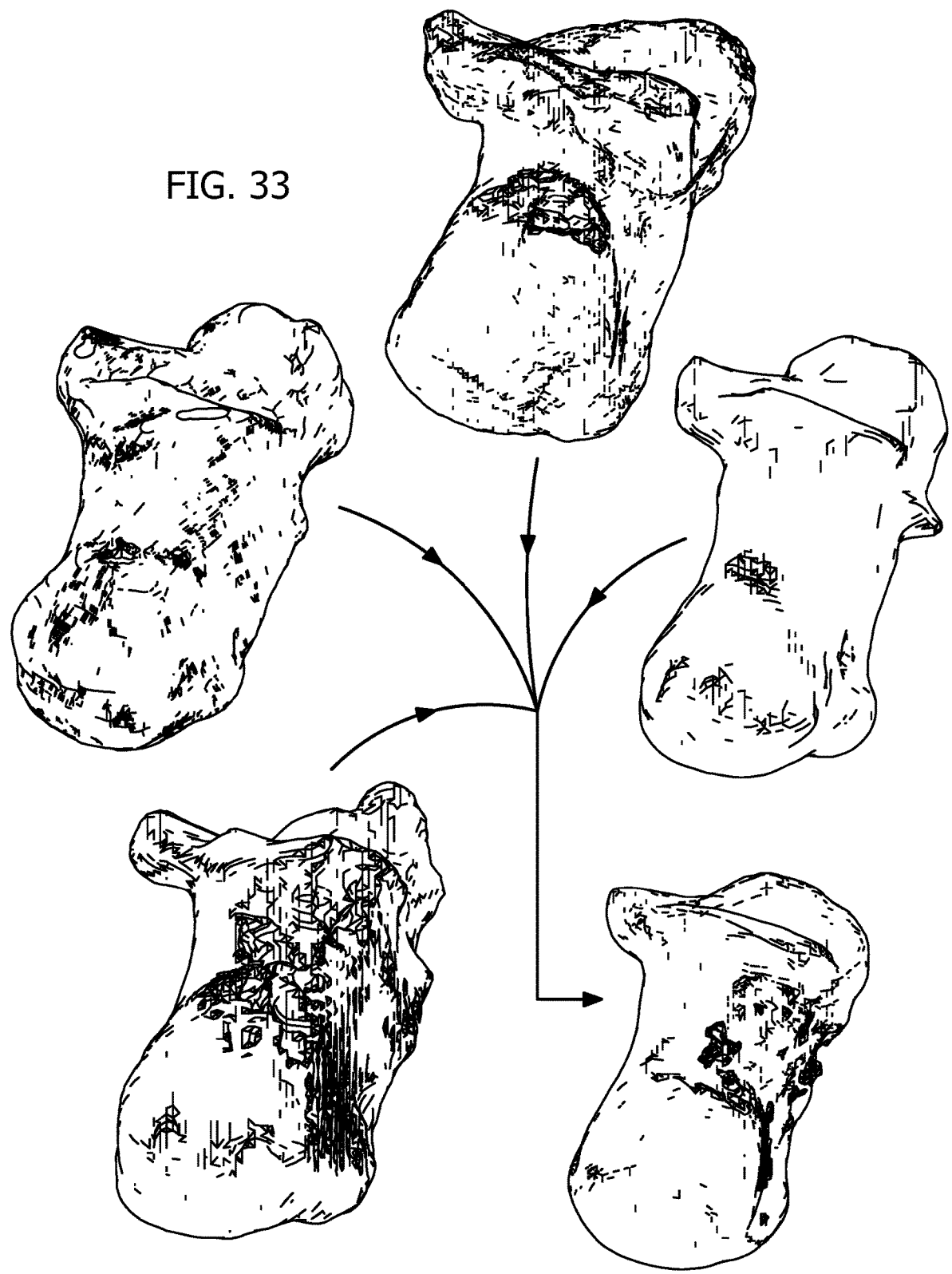

FIG. 33 illustrates four distinct calcanei (heel bones) that are inputs into an algorithm that results in an exemplar model as the average resultant of the four original inputs.

Figure 34:
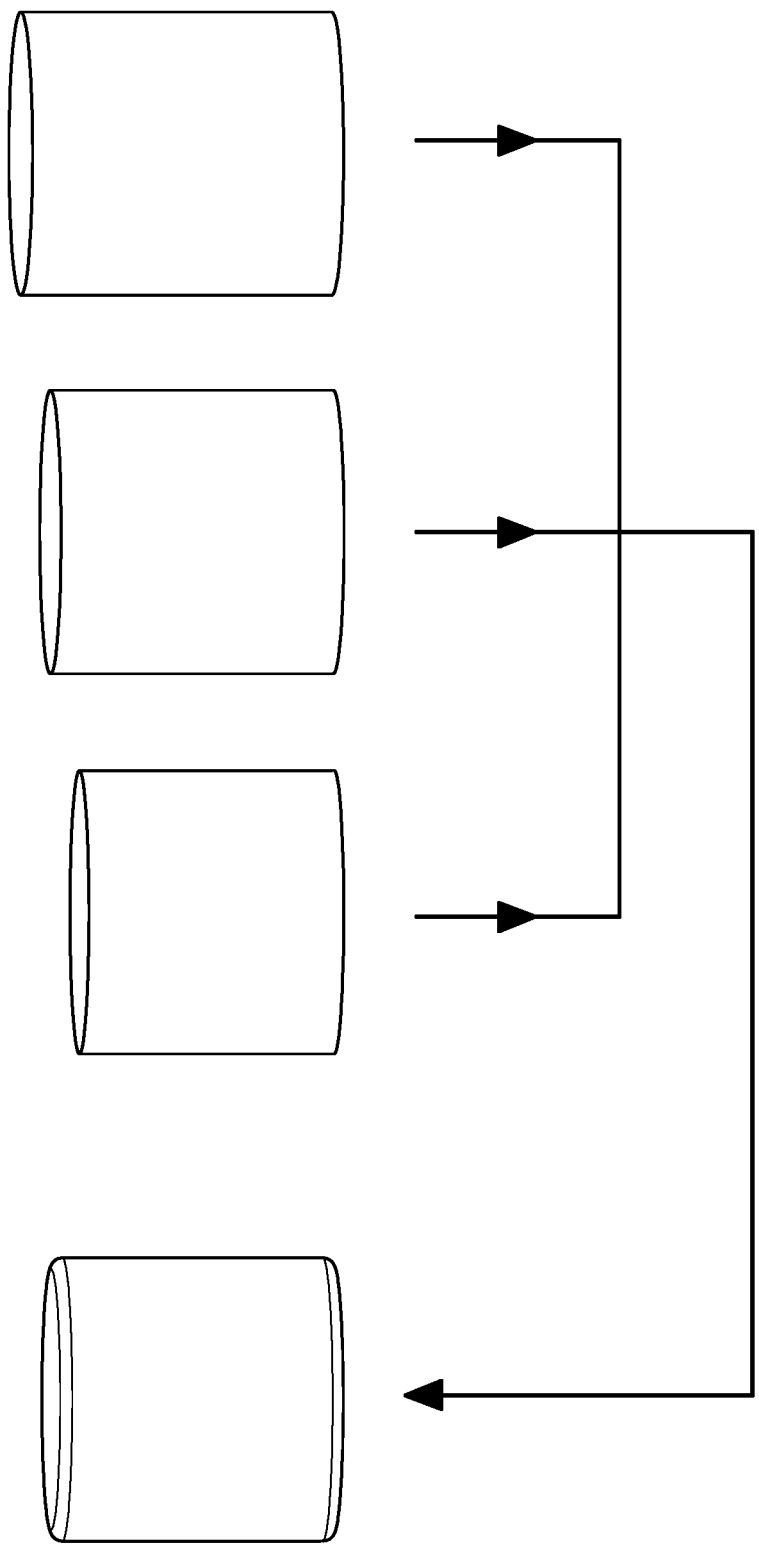

FIG. 34 illustrates three distinct cylinders that are inputs into an algorithm that results in an exemplar model as the average resultant of the three original inputs.

DETAILED DESCRIPTION OF THE INVENTION

Embodiments of the invention are described below and are shown in the figures of the drawing.

The steps of manufacturing processes of at least one invention disclosed herein are as follows:

Step 1 involves determining the one or more surgeries to be practiced on one or more simulators and determining the type of patient profile that the simulator is to be based upon. Some simulators can be used for several kinds of surgical operations. For example, where a surgical simulator is to be made is to train for cervical spine fusions and disc replacements due to cervical disc herniations, the patient profile of interest could be a young, Asian male, with an average BMI, average build and no prior cervical neck injuries or conditions.

Step 2: Acquire de-identified CT Scans and MRI Scans of the surgical site of interest, and condition/injury of interest, based on the desired patient profile/demographic of interest to build the 3D model of the surgical simulator. For the example in Step 1, the scans would be of the cervical spine of Asian males that are within the same age cohort, have similar physical attributes, and may or may not include the injury of interest, in this case a cervical disc herniation.

Step 3: For each radiology report, create an STL for each desired anatomical structure and tissue to be replicated in the simulator using a technique called segmentation. The software to be used includes but is not limited to Materialise Mimics, Slicer, itk-SNAP and equivalents. The end result is a three dimensional model of the desired surgical site for each scan, with variations stemming from variations in the patients/cadavers that the radiology scans are sourced from. Continuing with the provided example, if three scans were being used, then each scan will be segmented to ultimately create two or more sets of STLs that constitute the anatomy and tissues of the surgical site of interest, that being the neck. Each scan provides a set anatomical components in the form of STLs, including pertinent nerves, vascular structures, tissue layers, membranes, cartilage structures and muscles.

Step 4) Because the three-dimensional models are sourced from individuals, the anatomical structures, tissues, and spatial positioning may not be representative of the population that the simulator is supposed to represent. Therefore, each STL of each specific anatomical component will be averaged together into a single exemplar STL, using software including but not limited to Geomagic Wrap and equivalents and/or a custom made algorithm for STL averaging. The end result is an exemplar STL for each component of the simulator made from STLs sourced from the scans of individuals. The process is repeated for each anatomical STL component until the final result is a singular exemplar of the surgical site of interest, made of STLs that are derived from individuals, but averaged to represent the profile of interest more accurately by removing individual nuances. For the example provided in step one, from three sets of STLs made in step three, an exemplar for each anatomical component that makes up the simulator will be created by averaging the characteristics of each STL, including size, shape, and orientation. Thus, there are three distinct STLs of the human C1 vertebra from the segmented scans, one from each source. To make an average model of the C1 vertebra for the patient profile desired, each STL is averaged together to create a singular C1 vertebra that is not directly sourced from an individual and more accurately represents the patient profile that is of interest. This process is then applied to every anatomical STL component.

Step 5) Modify the exemplar three-dimensional model as desired in order to customize patient variables, surgical variables, and spatial arrangements. The software to do so includes but is not limited to Meshmixer and Blender. Continuing with example provided in Step 1, if the exemplar model of the surgical site does not have the injury to be practice upon, then the cervical disc herniation can be added by editing the STLs that make up the model. If one wants to include the condition of cervical fracture to practice having that variable, then the STLs of the vertebrae can be edited directly to have fractures of varying intensity or location depending on desire.

Step 6) Three dimensionally print the STLs of the anatomical components that make up the simulator using a variety of three-dimensional printers that can best produce the components with high resolution, and in biofidelic materials. This is done through an operation called Slicing. STLs are the three dimensional models to be made, and slicing is the instruction for the machine on how to three dimensionally print said models. Slicing is specifying how a component will be printed, by defining a variety of parameters including but not limited to, materials used, density, flexibility, shore hardness, dimensional resolution, perimeter thickness, and directionality of material deposition. These slicing parameters affect how a material behaves, which then can control how well a material mimics a biological tissue. Slicing software include but are not limited to Simplify3D, GrabCAD, and Slic3r. After slicing a STL, the end result is G-Code, which are instructions to a 3D printer specifying what is to be made and how it is to make it. Each STL of the simulator is sliced to specification, and then three dimensionally printed on the machine best meeting its demands. Continuing with the example from Step 1, components of the cervical spine surgery simulator include the vertebrae of the cervical spine and the discs in between them. These require different materials and properties, and therefore different slicing settings. Because of these settings and material parameters, different three dimensional printers generally should be used. For the vertebrae, the most similar material to cancellous bone might be PEEK, and so a three dimensional printer capable of printing PEEK should be used. For the cervical discs, a soft, flexible material must be used, such as TPU or PCU. And so a 3D printer capable of three dimensionally printing flexible filaments should be used for making discs. It is also possible that a multi-material printer can print the vertebrae and the cervical discs, in their respective materials, as one object using the 3D interlacing technique. Slicing settings can differ from component to component to best match the design and demands of the simulator being manufactured. If the surgical simulator is designed for operations involving only the C2 vertebra and the C3 vertebra, then only those vertebrae need to be sliced and 3D printed in PEEK. The rest of the cervical spine vertebrae can be sliced and printed in another material like PLA because those components are not designed to be directly operated on and therefore do not require the same level of bio-fidelity.

Step 7) Assemble the completed three dimensional models together to complete the surgical simulator. Due to separately manufactured anatomical components, the modularity of the simulator allows for replacement of components rather than the entire unit and different variables of interest can be implemented in the simulator by swapping out components of the same anatomical structure/tissue with those that are printed with different characteristics. Further with the example of one embodiment, after the cervical spine surgery simulator is assembled and used, there is a desire to practice the operations with certain variables, and so the patient profile is changed to include obesity and osteopenia, that is low bone density. Then components pertinent to those conditions, such as the subcutaneous layer and vertebrae respectively, are to be reprinted to reflect those new variables. In this case, the subcutaneous layer can be made thicker to reflect the higher BMI, and the vertebrae can be printed with a lower density to reflect the osteopenia. These new components can simply be placed where the old ones used to be.

This manufacturing process is new in part because the three-dimensional models are not sourced from an individual, but from several individuals of similar biological/demographic profile, allowing more accurate representation of a certain subpopulation's anatomy. Furthermore, this manufacturing process allows for full customization of the simulator to replicate surgical variables of interest due to its use of directly three dimensionally printing the components of the simulator. For example, if one wanted to practice doing gallbladder removal on an obese patient, then the subcutaneous layer can be increased and adjusted to match that patient variable.

A novelty is the ability to use multiple materials of different biofidelic properties in a single three-dimensional printed component, unlike most other manufacturing processes involve creating a mold that cannot be modified and is limited to a single type of material. Another novelty is that the anatomical components of the simulators can be printed separately, so modularity is another key component. Replaceable parts allow for continued use after damaged components are reprinted, and for adjustment of component properties, including but not limited to size, shape, materials used, and density.

Alternative Steps (Labeled "b" and "c" steps):

Step 2b) Replacing Steps 2) through 4), instead of sourcing the models from actual CT and MRI scans and averaging them into an exemplar, the process allows for the purchase and/or download of available anatomical models online to slice and 3D print. This has several consequences:

First, surrounding tissue STLs (like fat, skin, or fascia, that don't have clear shapes/structures) are not available online, and therefore must be CAD modeled to fit STLs sourced online. This loses spatial accuracy and relativity.

Sourcing STLs from online means that individualistic conditions and characteristics pervade into the model, meaning that the final simulator cannot be generalizable.

Online STLs are Often Poor Resolution

Different anatomical STLs are difficult/near impossible to assemble when they come from different sources. For example, a heart STL from one source may be too big or misshapen to fit between a STL of lungs from another source. Assembling differently sourced STLs (unlike merging/averaging differently sourced STLs into a single, coherent set) is like creating Frankenstein's monster. So, the resulting simulator would not be accurately reflective of actual human anatomy because its components do not fit well together.

Step 6b) 3D Print molds of STLs instead of the STLs themselves. This issues about 3D printing molds are:

It is wasteful in terms of time and material, since each mold can only produce one component. This also inhibits modularity of components for the simulators. Furthermore, molds only allow for one kind of material to be used, which is not biologically accurate to certain anatomy. For example, a layer of tissue in a model might be comprised of both muscle and connective tissue. That layer would need to be made of two different materials; one to mimic the muscle and another for the connective tissue. A mold generally cannot use multiple materials on a single component, so it would have to choose to either mimic the muscle or mimic the connective tissue. A three-dimensional printer, being an additive manufacturing process, can add as many materials into a component as necessary in whatever distribution it wants. A mold is homogenous, human anatomy rarely is. Furthermore, production using molds cannot adjust density to the same degree as three-dimensional printing.

Biofidelic materials to mimic soft tissues are available for molds, but polymers to mimic hard tissue like bone generally require injection molding, which requires custom metal molds to be made. That is prohibitively expensive and removes the aspect of variability in the simulator, since components cannot be adjusted and remade to desire as easily as three-dimensional printing.

Step 6c) Replacing Steps 6) through 7), an alternative to printing the simulator components on a variety of printers, is that the entire simulator can be printed at once. All anatomical structures and their surrounding tissues are all printed together on the same machine. Limitations of these replacement steps include:

Lack of Material Variety, and Therefore Poorer Representation of Biological Tissues.

Staggered manufacturing flow. If the print job fails, then the entire job has to be restarted. Various printers for various components running simultaneously compartmentalize the consequences of job failures and printer malfunctions to individual components, which does not disrupt manufacturing flow to the same degree.

Surgical Training for Medical Schools and Residency Programs.

Possible experiments include implementing simulators that are manufactured from this process to medical schools and residency programs to see if there is an improvement in surgical skills/performance corresponding to the surgery that the simulator is meant to model. Other experiments include measuring changes in comfort, confidence, and speed in performing an operation if one has been trained in using a simulator previously versus an individual who does not have practice from the model.

This manufacturing process creates simulators that can train a wide variety of surgical operations with numerous combinations of variables, which is useful for surgical training, especially for operations that are rare and previously difficult to gain experience in.

Analytical steps that are related to the process are primarily involved with the segmentation of radiology images and the generation of the corresponding STLs. Segmentation involves stacking CT or MRI scans to generate a three-dimensional volume, and then analyzing different tissue densities in order to differentiate anatomical structures and bodies. Additional analytical processes include the averaging of the STLs, which involves using specific software and/or algorithms to measure the dimensions, shape, and structures of the STLs in order to average those individual STLs into a single exemplar. The final analytical step is the Slicing process in order to generate G-Code for the 3D printers to follow. This involves specifying what is being printed, meaning an exemplar STL, and how it will be printed, by setting certain parameters including but not limited to material type, density, layer height, shell thickness, and material deposition patterns.

The manufacturing process is modeled this way because the goal is to go from 2D images via radiology reports, to a full, physical three-dimensional object comprised of various physical three-dimensional components made of differing materials. The process starts with actual radiology scans because CAD modeling anatomy is very difficult/near impossible for complex structures.

The dimensions, and shapes of human anatomical structures are not readily available in literature, which means that modeling from scratch would lead to inaccurate STLs that do not truly reflect human anatomy. Plus, measures of relative spatiality between anatomical structures are also lacking in literature. Furthermore, for my invention it is generally preferred not ti source STLs of anatomy available online because they are often poor in resolution, inaccurate in form, or segmented from a single individual's radiology scan which is not reflective of the population a simulator would be designed to model. The inventions disclosed herein involve removing individualistic features and characteristics of anatomy to best have the simulator reflect patient profiles of interest.

Ultimately, the process of one embodiment starts with individual scans that are segmented to make corresponding sets of anatomical STLs (for model accuracy), which are then averaged into an exemplar set of STLs (for patient profile accuracy), which are then modified for desired conditions/injuries (for what variables/type of operation the simulator is designed to train), which are then sliced to make G-Code (for tissue behavior accuracy/biofidelity), which are then three dimensionally printed using a variety of printers (for different materials use, and printing techniques.), which then the three dimensional components are assembled to create the full model. Creating multiple components to be assembled instead of doing a singular print allows for multiple material use to mimic a variety of tissues, allows for modularity to change training variables by changing certain parts, and allows for replacement of damaged/expended parts. Also, this process allows for manufacturing flow to continue in case a printer fails, because only one part needs to be reprinted instead of having the entire simulator production job be restarted.

The overall algorithm of an exemplary embodiment follows spherical coordinates by: 1) designating the center of every STL (which generally is the exact middle of the file); 2) for multiple angles (e.g. basically combination of longitude and latitude) calculate the average radius at the angle for all of the given stls. The interval of angles are customizable degree increments. For example, it could by 360*180 sectors (e.g. longitude/latitude squares). Integrals and other methods may also be used. The NumPy-stl python library provides a good set of functions and procedures that are adoptable for these purposes.

Another process that may be substituted and/or used in conjunction with the above-described embodiment involves using a Signed Distance Function (SDF), which is a function that maps a coordinate in 3D space to the shortest distance between the coordinate and a 3D surface (in this case, the anatomical component of interest). The SDF's sign depends on whether the coordinate is inside or outside the object STL. The SDF is able to be constructed and/or reconstructed from an object using a straightforward projection calculation to calculate the closest point on the surface to every point.

Using the SDF procedure, for all the given STL files, the SDF is calculated for each one. Then, each of the SDFs are averaged together, including the sign. The result is an average distance to collection of STLs from every given point in a 3D coordinate system. From there, given the average SDF, an object is constructed (or reconstructed) using an algorithm known as Marching Cubes or its equivalent. When complete, the resultant object can be healed and smoothed out using standard STL software to fix unnatural irregularities and noise.

Furthermore, in an alternative embodiment, an input is a set of STL mesh files or equivalent and the output is an STL mesh file or equivalent that reflects the average composition of each of the input files. The inventor has had success with alternative embodiment using python 3 with an anaconda distribution and the following imports:

```
Trimesh (storing and manipulating meshes) is cited as:
@software{trimesh,
  author = {{Dawson-Haggerty et al.}},
  title = {trimesh},
  url = {https://trimsh.org/},
  version = {3.2.0},
  date = {2019-12-8},
}
```

Trimesh is a Python library for loading and using triangular meshes with an emphasis on watertight surfaces. The stated goal of the library is to provide a full featured and well tested Trimesh object which allows for easy manipulation and analysis, in the style of the Polygon object in the Shapely library. Trimesh provides the following features:

Import meshes from binary/ASCII STL, Wavefront OBJ, ASCII OFF, binary/ASCII PLY, GLTF/GLB 2.0, 3MF, XAML, 3DXML, etc.
Import and export 2D or 3D vector paths from/to DXF or SVG files
Import geometry files using the GMSH SDK if installed (BREP, STEP, IGES, INP, BDF, etc)
Export meshes as binary STL, binary PLY, ASCII OFF, OBJ, GLTF/GLB 2.0, COLLADA, etc.
Export meshes using the GMSI SDK if installed (Abaqus INP, Nastran BDF, etc)
Preview meshes using pyglet or in-line in jupyter notebooks using three.js
Automatic hashing of numpy arrays for change tracking using MD5, zlib CRC, or xxhash
Internal caching of computed values validated from hashes
Calculate face adjacencies, face angles, vertex defects, etc.
Calculate cross sections, i.e. the slicing operation used in 3D printing
Slice meshes with one or multiple arbitrary planes and return the resulting surface
Split mesh based on face connectivity using networkx, graph-tool, or scipy.sparse
Calculate mass properties, including volume, center of mass, moment of inertia, principal components of inertia vectors and components
Repair simple problems with triangle winding, normals, and quad/tri holes
Convex hulls of meshes
Compute rotation/translation/tessellation invariant identifier and find duplicate meshes
Determine if a mesh is watertight, convex, etc.
Uniformly sample the surface of a mesh
Ray-mesh queries including location, triangle index, etc.
Boolean operations on meshes (intersection, union, difference) using OpenSCA) or Blender as a back end. Note that mesh booleans in general are usually slow and unreliable
Voxelize watertight meshes
Volume mesh generation (TETgen) using Gmsh SDK
Smooth watertight meshes using Laplacian smoothing algorithms (Classic, Taubin, Humphrey)
Subdivide faces of a mesh
Minimum volume oriented bounding boxes for meshes
Minimum volume bounding spheres
Symbolic integration of functions over triangles
Calculate nearest point on mesh surface and signed distance
Determine if a point lies inside or outside of a well-constructed mesh using signed distance
Primitive objects (Box, Cylinder, Sphere, Extrusion) which are subclassed Trimesh objects and have all the same features (inertia, viewers, etc)
Simple scene graph and transform tree which can be rendered (pyglet window, three.js in a jupyter notebook, pyrender) or exported.
Many utility functions, like transforming points, unitizing vectors, aligning vectors, tracking numpy arrays for changes, grouping rows, etc.

--- skimage (implementation of marching cubes) can be cited as:
@article{van2014scikit,
title={scikit-image: image processing in Python},
author={Van der Walt, Stefan and Sch{\"o}nberger, Johannes L and Nunez-Iglesias, Juan and Boulogne, Fran{\c{c}}ois and Warner, Joshua D and Yager, Neil and Gouillart, Emmanuelle and Yu, Tony}, -continued

```
    journal={PeerJ},
    volume={2},
    pages={e453},
    year={2014},
    publisher={PeerJ Inc.}
}
scikit-image (a.k.a. skimage) is Image Processing for Python through is a collection of
algorithms for image processing and computer vision.
NumPy (general vector/matrix arithmetic) is generally cited as:
@Article{harris2020array,
title = {Array programming with {NumPy}},
author = {Charles R. Harris and K. Jarrod Millman and St{\'{e}}fan J.
    van der Walt and Ralf Gommers and Pauli Virtanen and David
    Cournapeau and Eric Wieser and Julian Taylor and Sebastian
    Berg and Nathaniel J. Smith and Robert Kern and Matti Picus
    and Stephan Hoyer and Marten H. van Kerkwijk and Matthew
    Brett and Allan Haldane and Jaime Fern{\'{a}}ndez del
    R{\'{i}}o and Mark Wiebe and Pearu Peterson and Pierre
    G{\'{e}}rard-Marchant and Kevin Sheppard and Tyler Reddy and
    Warren Weckesser and Hameer Abbasi and Christoph Gohlke and
    Travis E. Oliphant},
year = {2020},
month = sep,
journal = {Nature},
volume = {585},
number = {7825},
pages = {357--362},
doi = {10.1038/s41586-020-2649-2},
publisher = {Springer Science and Business Media {LLC}},
url = {https://doi.org/10.1038/s41586-020-2649-2}
}
```

NumPy is a fundamental package for scientific computing in Python. NumPy arrays facilitate advanced mathematical and other types of operations on large numbers of data.

```
mesh-to-sdf (implementation of calculating the SDF voxel) can be cited as
@misc{remelli2020meshsdf,
    title={MeshSDF: Differentiable Iso-Surface Extraction},
    author={ Edoardo Remelli and Artem Lukoianov and Stephan R. Richter and Benoît Guillard
and Timur Bagautdinov and Pierre Baque and Pascal Fua},
    year={2020},
    eprint={2006.03997},
    archivePrefix={arXiv},
    primaryClass={cs.CV}
}
```

Mesh-to-sdf calculates approximate SDFs for triangle meshes. It works for non-watertight meshes (meshes with holes), self-intersecting meshes, meshes with non-manifold geometry, and meshes with inconsistently oriented faces. It has the following common parameters.

surface_point_method: The method to generate a surface point cloud. Either 'scan' or 'sample'. The scanning method creates virtual scans while the sampling method uses the triangles to sample surface points. The sampling method only works with watertight meshes with correct face normals, but avoids some of the artifacts that the scanning method creates.

sign_method: The method to determine the signs of the SDF values. Either 'normal' or 'depth'. The normal method uses normals of the point cloud. The normal method generally works better for meshes with holes, but sometimes results in "bubble" artifacts. The depth method avoids the bubble artifacts but is less accurate.

bounding_radius: The radius of a sphere that contains all mesh vertices. If none, this value is calculated using the mesh.

scan_count: Number of scans when using the scanning method scan_resolution: Resolution for the scans in pixels.

sample_point_count: Number of points to sample when using surface_point method='sample' normal_sample_count: Number of nearby surface points to check when using sign_method='normal'. The sign of the resulting SDF is determined by majority vote.

In this further example embodiment, the following algorithm design is used:

Step 1: Each mesh is loaded into the program as a trimesh with the python Trimesh package.

Trimeshes store objects as a set of vertices and a list of triplets of vertices connected by faces.

Step 2: Certain inputs are given in millimeters, others are given in inches. Depending on the input given, the input mesh is converted to inches. This transformation is currently applied to all inputs, so the algorithm is not coded to mix and match inputs in different units. However, this could be handled by a processor operating an algorithm that coverts the units before, after and/or during input.

Step 3: Each object is centered, so that the centroid of the object lies at the origin of the coordinate plane. There are two types of centroids explored: a centroid derived from the object mass itself and a centroid derived from the bounding box enclosing the object. More information can be found in the Tuned Parameters section.

Step 4: The Signed Distance Function (SDF) of each mesh is calculated at a resolution, such as 100 pixels.

Essentially, at 100×100×100 point on the 3d object, the vector (which encodes the distance and direction) from that point to the nearest surface point of the mesh is stored. The pixel resolution another tunable parameter.

Step 5: The resultant SDF voxels are averaged together, coordinate by coordinate. If the user provides weights for each input mesh, a weighted average can be calculated, though by default the arithmetic mean is used.

Step 6: The Marching Cubes algorithm is applied from the Skimage package to reconstruct a mesh from the given averaged voxel.

Step 7: The resultant mesh is healed by removing any extraneous surfaces created by Marching Cubes. Only the largest contiguous surface is kept.

Step 8: Since the Marching Cubes output is not scaled properly, it must be scaled to match the input sizes. The average mesh is scaled to meet the average size of the inputs, as detailed in the "Final Scaling" section of tuned parameters.

Step 9: The final average mesh is then exported as an .stl file.

Tuned Parameters

Centroid

Input samples are not presumed to be aligned. To account for this, each input mesh is centered upon loading in by subtracting the centroid of that object from each vertex coordinate. However, there are two distinct ways to calculate the centroid of an object, and thus two distinct ways of centering meshes. One method is calculating the exact center of the bounding box of the object: the smallest rectangular prism that fully encloses the object. The other method is by directly calculating the centroid of the object using the Trimesh package. Though the two do not differ significantly, the direct centroid respects the variable density of the original object while the bounding box centroid respects the extremities.

Final Scaling

Objects created from the skimage implementation of marching cubes are not properly scaled to the size of the inputs. Therefore, scaling of the average is done manually. The mesh average is thus scaled to the average sizes of each input, equally weighted unless otherwise denoted. Two metrics are used to establish the sizes of the inputs. The first metric is volume; the average mesh is scaled to have volume equal to the average volume of the inputs. The second metric is the normalized distance of a mesh, or the Euclidean distance from the center of the mesh to the farthest vertex. Both metrics work, but the volume metric is generally preferred as the normalized metric tends to create slightly larger average meshes than expected.

Marching Cubes Resolution

This value is the resolution of the voxels calculated from each input mesh. It is tuned to be 100. Higher values tend to crash the program. The inventor has also had success running at 64 resolution.

Visualizations

As set forth in the figure descriptions above, the figures of the drawings section provide visualizations of the outputs of the various methods described herein and corresponding lattice forms to enable three-dimensional printing and bonding of various materials and objects into integrated parts.

The methods, systems, processes, lattice bonding, and other inventions disclosed herein have applicability to medical devices, implants, and other fields and trade that would be recognized by persons with ordinary skill in the arts. For instance, the same methods, systems, processes, lattice bonding, and other inventions can generate not only anatomical parts but also other anatomical parts such as prosthesis for use in surgery and replacement of damaged and/or lost limbs and organs.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A three-dimensional anatomical part comprising:
   one or more materials three-dimensionally printed from averaged data generated from three-dimensional image data gathered from more than one source wherein the averaged data comprises an average of one or more set of select characteristics of the three-dimensional image data; and,
   wherein the select characteristics are mean averaged by radius length from each source from the three-dimensional image data corresponding to the select characteristics measured from the center of each individual source of three-dimensional image data by radian intervals wherein for each radian interval the lengths are summed and divided by the total number of sources for the three-dimensional image data corresponding to the select characteristics.

2. The three-dimensional anatomical part of claim 1 wherein the select characteristics further comprise one or more disease structures.

3. The three-dimensional anatomical part of claim 1 wherein the averaged data is altered by modifying one or more of the select characteristics.

4. The three-dimensional anatomical part of claim 1 wherein the averaged data contains multiple lengths at one or more single radian interval representing one or more of different materials and different structures wherein at least one of the lengths at the one or more single radian interval begins at a distance from the center of the source three-dimensional image data.

5. The three-dimensional anatomical part of claim 1 wherein the averaged data is altered by modifying one or more of the select characteristics wherein at least one of the select characteristics modified relates to one or more of lengths, different materials and different structures beginning at a distance from the center of the three-dimensional source image data.

6. The three-dimensional anatomical part of claim 1 wherein the anatomical parts generated are surgical trainers.

7. The three-dimensional anatomical part of claim 1 wherein the anatomical parts generated are prosthesis.

8. A system for creating three dimensional anatomical parts comprising:
   a scanner that scans parts from more than one source;
   an indexer that creates one or more indices of the data for the scanned parts by a set of characteristics;
   an identification module that determines the parts in the indices corresponding with select characteristics from the set of characteristics;
   an averaging module that uses data corresponding to more than one source matching the select characteristics to create averaged data;

a rendering module that uses the averaged data to generate one or more anatomical parts; and, wherein the select characteristics are mean averaged by radius length from each source from the three-dimensional image data corresponding to the select characteristics measured from the center of each individual source of three-dimensional image data by radian intervals wherein for each radian interval the lengths are summed and divided by the total number of sources for the three-dimensional image data corresponding to the select characteristics.

9. The system of claim 8 wherein the rendering module generates one or more anatomical parts from the averaged data by three-dimensional printing.

10. The system of claim 8 wherein the rendering module generates one or more anatomical parts from the averaged data by virtual computer rendered model.

11. The system of claim 8 wherein the rendering module generates one or more anatomical parts from the averaged data by generating a three-dimensional mold wherein the mold is the inverse of a three-dimensional part described by the averaged data.

12. A method of creating three dimensional anatomical parts comprising, via at least one processor:
    gathering three-dimensional image data for parts from more than one source;
    indexing the image data from each source by a set of characteristics;
    selecting select characteristics from the set of characteristics;
    using an SDF procedure to create averaged data corresponding to the three-dimensional image data for parts from more than one source wherein the select characteristics are averaged by radius length from each source from the three-dimensional image data corresponding to the select characteristics measured from the center of each individual source of three-dimensional image data by radian intervals wherein for each radian interval the lengths are summed and divided by the total number of sources for the three-dimensional image data corresponding to the select characteristics; and
    using the averaged data to generate one or more anatomical parts.

13. Three-dimensional anatomical parts created by averaging parts gathered from more than one source comprising:
    one or materials three-dimensionally printed from averaged data generated from three-dimensional image data gathered from more than one source DICOM scans wherein the averaged data comprises an average of one or more set of select characteristics of the three-dimensional image data;
    wherein the select characteristics are mean averaged by radius length from each source from the three-dimensional image data corresponding to the select characteristics measured from the center of each individual source of three-dimensional image data by radian intervals wherein for each radian interval the lengths are summed and divided by the total number of sources for the three-dimensional image data corresponding to the select characteristics; and,
    population averaging is used to create both external and internal geometries of the three-dimensional anatomical parts.

* * * * *